(12) United States Patent
Li et al.

(10) Patent No.: US 10,893,674 B2
(45) Date of Patent: *Jan. 19, 2021

(54) EFFICIENT STABILIZER IN CONTROLLING SELF ACCELERATED DECOMPOSITION TEMPERATURE OF PEROXYCARBOXYLIC ACID COMPOSITIONS WITH MINERAL ACIDS

(71) Applicant: Ecolab USA Inc., Saint Paul, MN (US)

(72) Inventors: Junzhong Li, Eagan, MN (US); David D. McSherry, St. Paul, MN (US); Richard Staub, Lakeville, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/019,050

(22) Filed: Feb. 9, 2016

(65) Prior Publication Data

US 2016/0150779 A1 Jun. 2, 2016

Related U.S. Application Data

(63) Continuation of application No. 14/584,148, filed on Dec. 29, 2014, now Pat. No. 9,288,992, which is a continuation of application No. 13/785,044, filed on Mar. 5, 2013, now abandoned.

(51) Int. Cl.

| A61L 2/18 | (2006.01) |
|---|---|
| A01N 59/00 | (2006.01) |
| A01N 25/22 | (2006.01) |
| A01N 37/02 | (2006.01) |
| A01N 37/16 | (2006.01) |
| A01N 25/02 | (2006.01) |
| C02F 1/50 | (2006.01) |

(52) U.S. Cl.
CPC ............. *A01N 37/16* (2013.01); *A01N 25/02* (2013.01); *A01N 25/22* (2013.01); *A01N 37/02* (2013.01); *A01N 59/00* (2013.01); *A61L 2/186* (2013.01); *C02F 1/50* (2013.01)

(58) Field of Classification Search
CPC ......... A61L 2/18; A61L 2/186; C07C 409/24; C07C 409/26; C07C 407/06; C07D 213/79; A01N 59/00; A01N 25/22; A01N 37/02; A01N 37/16; A01N 43/40
USPC ................... 424/616; 422/28; 562/2, 3, 4, 6; 568/568
See application file for complete search history.

(56) References Cited

U.S. PATENT DOCUMENTS

| 2,609,391 A * | 9/1952 | Greenspan .......... C07C 407/006 562/3 |
|---|---|---|
| 2,955,905 A | 10/1960 | Davies et al. |
| 3,053,633 A | 9/1963 | Dunlop |
| 3,130,169 A | 4/1964 | Blumbergs |
| 3,156,654 A | 11/1964 | Konecny |
| 3,256,198 A | 6/1966 | Matzner |
| 3,272,750 A | 9/1966 | Chase |
| 3,414,593 A | 12/1968 | Robson |
| 3,432,546 A | 3/1969 | Oringer et al. |
| 3,847,830 A | 11/1974 | Williams et al. |
| 3,925,234 A | 12/1975 | Hachmann et al. |
| 3,956,159 A | 5/1976 | Jones |
| 3,969,258 A | 7/1976 | Carandang et al. |
| 4,003,841 A | 1/1977 | Hachmann et al. |
| 4,013,575 A | 3/1977 | Castrantas et al. |
| 4,051,058 A | 9/1977 | Böwing et al. |
| 4,051,059 A | 9/1977 | Bowing |
| 4,100,095 A | 7/1978 | Hutchins et al. |
| 4,126,573 A | 11/1978 | Johnston |
| 4,129,517 A | 12/1978 | Eggensperger et al. |
| 4,144,179 A | 3/1979 | Chatterji |
| 4,170,453 A | 10/1979 | Kitko |
| 4,233,235 A | 11/1980 | Camden et al. |
| 4,259,201 A | 3/1981 | Cockrell, Jr. et al. |
| 4,297,298 A | 10/1981 | Crommelynck et al. |
| 4,311,598 A | 1/1982 | Verachtert |
| 4,367,156 A | 1/1983 | Diehl |
| 4,370,251 A | 1/1983 | Liao et al. |
| 4,374,035 A | 2/1983 | Bossu |
| 4,391,723 A | 7/1983 | Bacon et al. |
| 4,391,724 A | 7/1983 | Bacon |
| 4,412,934 A | 11/1983 | Chung et al. |
| 4,430,236 A | 2/1984 | Franks |
| 4,470,919 A | 9/1984 | Goffinet et al. |
| 4,473,507 A | 9/1984 | Bossu |

(Continued)

FOREIGN PATENT DOCUMENTS

| CA | 2084172 | 6/1993 |
|---|---|---|
| CA | 2152908 | 7/1997 |

(Continued)

OTHER PUBLICATIONS

Parker et al. J. Org. Chem. 1955, 77, 4037-4041.*
Korean Intellectual Property Office, PCT/IB2011/055832 filed Dec. 20, 2011, The International Search Report and the Written Opinion of the International Searching Authority, dated Aug. 14, 2012, 14 pages, Aug. 14, 2012.
Korean Intellectual Property Office, PCT/IB2011/055830 filed Dec. 20, 2011, "The International Search Report and the Written Opinion of the International Searching Authority", dated Aug. 24, 2012, 8 pages, Aug. 24,2012
Yin, De Lu (Tyler). et al., "Switching catalysis from hydrolysis to perhydrolysis in P. fluorescens esterase", Biochemistry, vol. 49, No. 9, (Mar. 9, 2010), pp. 1931-1942, Mar. 9, 2010.

(Continued)

*Primary Examiner* — Irina Neagu
(74) *Attorney, Agent, or Firm* — McKee, Voorhees & Sease, PLC

(57) ABSTRACT

Highly acidic, stabilized peroxycarboxylic acid compositions are disclosed as having both improved antimicrobial efficacy in comparison to conventional peroxyoctanoic acid and peroxyacetic acid compositions for sanitizing applications, and improved transport and shipping stability. In particular, low odor and low/no VOC compositions having dual functionality as both acid wash and sanitizing compositions are disclosed.

13 Claims, 4 Drawing Sheets

(56) References Cited

U.S. PATENT DOCUMENTS

| | | |
|---|---|---|
| 4,486,327 A | 12/1984 | Murphy et al. |
| 4,529,534 A | 7/1985 | Richardson |
| 4,540,721 A | 9/1985 | Staller |
| 4,587,264 A | 5/1986 | Joudan-Laforte et al. |
| 4,588,506 A | 5/1986 | Raymond et al. |
| 4,617,090 A | 10/1986 | Chum et al. |
| 4,655,781 A | 4/1987 | Hsieh et al. |
| 4,681,592 A | 7/1987 | Hardy et al. |
| 4,743,447 A | 5/1988 | Le Rouzic et al. |
| 4,778,618 A | 10/1988 | Fong et al. |
| 4,783,278 A | 11/1988 | Sanderson et al. |
| 4,786,431 A | 11/1988 | Broze et al. |
| 4,797,225 A | 1/1989 | Broze et al. |
| 4,846,992 A | 7/1989 | Fonsny |
| 4,853,143 A | 8/1989 | Hardy et al. |
| 4,879,057 A | 11/1989 | Dankowski et al. |
| 4,917,815 A | 4/1990 | Beilfuss et al. |
| 4,957,647 A | 9/1990 | Zielske |
| 4,964,870 A | 10/1990 | Fong et al. |
| 5,004,558 A | 4/1991 | Dyroff et al. |
| 5,019,292 A | 5/1991 | Baeck et al. |
| 5,030,240 A | 7/1991 | Wiersema et al. |
| 5,073,285 A | 12/1991 | Liberati et al. |
| 5,098,598 A | 3/1992 | Sankey et al. |
| 5,117,049 A | 5/1992 | Venturello et al. |
| 5,139,788 A | 8/1992 | Schmidt |
| 5,143,641 A | 9/1992 | Nunn |
| 5,160,656 A | 11/1992 | Carron et al. |
| 5,196,133 A | 3/1993 | Leslie et al. |
| 5,200,189 A | 4/1993 | Oakes et al. |
| 5,246,620 A | 9/1993 | Gethoffer et al. |
| 5,250,212 A | 10/1993 | de Buzzaccarini et al. |
| 5,250,707 A | 10/1993 | Inaba et al. |
| 5,264,229 A | 11/1993 | Mannig et al. |
| 5,266,587 A | 11/1993 | Sankey et al. |
| 5,268,003 A | 12/1993 | Coope et al. |
| 5,274,369 A | 12/1993 | Tsunoda et al. |
| 5,288,746 A | 2/1994 | Pramod |
| 5,296,239 A | 3/1994 | Colery et al. |
| 5,310,774 A | 5/1994 | Farrar |
| 5,314,687 A | 5/1994 | Oakes et al. |
| 5,349,083 A | 9/1994 | Brougham et al. |
| 5,362,899 A | 11/1994 | Campbell |
| 5,374,369 A | 12/1994 | Angevaare et al. |
| 5,382,571 A | 1/1995 | Granger et al. |
| 5,383,977 A | 1/1995 | Pearce |
| 5,391,324 A | 2/1995 | Reinhardt et al. |
| 5,398,506 A | 3/1995 | Martin |
| 5,409,629 A | 4/1995 | Shulman et al. |
| 5,422,028 A | 6/1995 | Oakes et al. |
| 5,431,849 A | 7/1995 | Damhus et al. |
| 5,433,881 A | 7/1995 | Townend et al. |
| 5,435,808 A | 7/1995 | Holzhauer et al. |
| 5,447,648 A | 9/1995 | Steindorf |
| 5,453,214 A | 9/1995 | van den Berg et al. |
| 5,463,112 A | 10/1995 | Sankey et al. |
| 5,464,563 A | 11/1995 | Moore et al. |
| 5,466,825 A | 11/1995 | Carr et al. |
| 5,472,619 A | 12/1995 | Holzhauer et al. |
| 5,486,212 A | 1/1996 | Mitchell et al. |
| 5,496,728 A | 3/1996 | Hardy et al. |
| 5,503,765 A | 4/1996 | Schepers et al. |
| 5,505,740 A | 4/1996 | Kong et al. |
| 5,525,121 A | 6/1996 | Heffner et al. |
| 5,545,374 A | 8/1996 | French et al. |
| 5,565,231 A | 10/1996 | Malone et al. |
| 5,576,282 A | 11/1996 | Miracle et al. |
| 5,589,507 A | 12/1996 | Hall, II et al. |
| 5,595,967 A | 1/1997 | Miracle et al. |
| 5,599,781 A | 2/1997 | Haeggberg et al. |
| 5,616,281 A | 4/1997 | Hardy et al. |
| 5,624,634 A | 4/1997 | Brougham |
| 5,632,676 A | 5/1997 | Kurschner et al. |
| 5,635,195 A | 6/1997 | Hall, II et al. |
| 5,637,755 A | 6/1997 | Nagumo et al. |
| 5,647,997 A | 7/1997 | Holzhauer et al. |
| 5,672,739 A | 9/1997 | Varadaraj et al. |
| 5,681,805 A | 10/1997 | Scheuing et al. |
| 5,683,977 A | 11/1997 | Jureller et al. |
| 5,698,506 A | 12/1997 | Angevaare et al. |
| 5,716,923 A | 2/1998 | MacBeath |
| 5,718,910 A | 2/1998 | Oakes et al. |
| 5,767,308 A | 6/1998 | Thiele et al. |
| 5,780,064 A | 7/1998 | Meisters et al. |
| 5,785,867 A | 7/1998 | LaZonby et al. |
| 5,814,592 A | 9/1998 | Kahn et al. |
| 5,817,614 A | 10/1998 | Miracle et al. |
| 5,827,447 A | 10/1998 | Tamura et al. |
| 5,827,808 A | 10/1998 | Appleby et al. |
| 5,840,343 A | 11/1998 | Hall, II et al. |
| 5,872,092 A | 2/1999 | Chan et al. |
| 5,880,083 A | 3/1999 | Beaujean et al. |
| 5,914,303 A | 6/1999 | Sankey et al. |
| 5,928,382 A | 7/1999 | Reinhardt et al. |
| 5,929,012 A | 7/1999 | Del Duca et al. |
| 5,965,033 A | 10/1999 | Huss et al. |
| 5,965,785 A | 10/1999 | Braden et al. |
| 5,968,885 A | 10/1999 | Del Duca et al. |
| 5,977,403 A | 11/1999 | Byers |
| 5,998,350 A | 12/1999 | Burns et al. |
| 6,010,729 A | 1/2000 | Gutzmann et al. |
| 6,022,381 A | 2/2000 | Dias et al. |
| 6,049,002 A | 4/2000 | Mattila et al. |
| 6,103,286 A | 8/2000 | Gutzmann et al. |
| 6,110,883 A | 8/2000 | Petri et al. |
| 6,136,769 A | 10/2000 | Asano et al. |
| 6,156,156 A | 12/2000 | Rousu et al. |
| 6,165,483 A | 12/2000 | Hei et al. |
| 6,177,393 B1 | 1/2001 | McGregor et al. |
| 6,183,763 B1 | 2/2001 | Beerse et al. |
| 6,183,807 B1 | 2/2001 | Gutzmann et al. |
| 6,207,632 B1 | 3/2001 | Brooker et al. |
| 6,211,237 B1 | 4/2001 | Huss et al. |
| 6,221,341 B1 | 4/2001 | Montgomery |
| 6,238,685 B1 | 5/2001 | Hei et al. |
| 6,262,013 B1 | 7/2001 | Smith et al. |
| 6,274,542 B1 | 8/2001 | Carr et al. |
| 6,277,804 B1 | 8/2001 | Kahn et al. |
| 6,284,793 B1 | 9/2001 | Fuchs et al. |
| 6,294,186 B1 | 9/2001 | Beerse et al. |
| 6,310,025 B1 | 10/2001 | Del Duca et al. |
| 6,326,032 B1 | 12/2001 | Richter et al. |
| 6,346,279 B1 | 2/2002 | Rochon |
| 6,384,008 B1 | 5/2002 | Parry |
| 6,399,564 B1 | 6/2002 | Speed et al. |
| 6,407,052 B2 | 6/2002 | Gassenmeier et al. |
| 6,417,151 B1 | 7/2002 | Grothus et al. |
| 6,432,661 B1 | 8/2002 | Heiffeld et al. |
| 6,436,885 B2 | 8/2002 | Biedermann et al. |
| 6,444,634 B1 | 9/2002 | Mason et al. |
| 6,503,876 B1 | 1/2003 | Broeckx et al. |
| 6,528,471 B1 | 3/2003 | Del Duca et al. |
| 6,537,958 B1 | 3/2003 | Di Capua et al. |
| 6,545,047 B2 | 4/2003 | Gutzmann et al. |
| 6,548,467 B2 | 4/2003 | Baker et al. |
| 6,548,470 B1 | 4/2003 | de Buzzaccarini et al. |
| 6,566,318 B2 | 5/2003 | Perkins et al. |
| 6,569,286 B1 | 5/2003 | Withenshaw et al. |
| 6,576,602 B1 | 6/2003 | Smerznak et al. |
| 6,589,565 B1 | 7/2003 | Richter et al. |
| 6,599,871 B2 | 7/2003 | Smith |
| 6,602,845 B2 | 8/2003 | Connor et al. |
| 6,607,710 B1 | 8/2003 | Ito et al. |
| 6,627,657 B1 | 9/2003 | Hilgren et al. |
| 6,635,286 B2 | 10/2003 | Hei et al. |
| 6,649,140 B2 | 11/2003 | Paparatto et al. |
| 6,686,324 B2 | 2/2004 | Ramirez et al. |
| 6,689,732 B1 | 2/2004 | Guedira et al. |
| 6,693,069 B2 | 2/2004 | Korber et al. |
| 6,696,093 B2 | 2/2004 | Ney et al. |
| 6,770,774 B2 | 8/2004 | Van De Bovenkamp-Bouwman et al. |
| 6,803,057 B2 | 10/2004 | Ramirez et al. |
| 6,806,246 B2 | 10/2004 | Preissner et al. |

(56) References Cited

U.S. PATENT DOCUMENTS

| | | |
|---|---|---|
| 6,830,591 B1 | 12/2004 | Wang et al. |
| 6,841,090 B1 | 1/2005 | Serego Allighieri et al. |
| 6,866,749 B2 | 3/2005 | Delmas et al. |
| 6,878,680 B2 | 4/2005 | Kitko et al. |
| 6,919,304 B2 | 7/2005 | Dykstra et al. |
| 7,012,053 B1 | 3/2006 | Barnabas et al. |
| 7,012,154 B2 | 3/2006 | Vineyard et al. |
| 7,060,136 B1 | 6/2006 | Zeiher et al. |
| 7,078,373 B2 | 7/2006 | Burrows et al. |
| 7,148,351 B2 | 12/2006 | Morris et al. |
| 7,169,236 B2 | 1/2007 | Zeiher et al. |
| 7,189,385 B2 | 3/2007 | Montgomery |
| 7,217,295 B2 | 5/2007 | Samain et al. |
| 7,243,664 B2 | 7/2007 | Berger et al. |
| 7,431,775 B2 | 10/2008 | Wang et al. |
| 7,448,255 B2 | 11/2008 | Hoots et al. |
| 7,494,963 B2 | 2/2009 | Ahmed et al. |
| 7,498,051 B2 | 3/2009 | Man et al. |
| 7,541,324 B2 | 6/2009 | Reinhardt et al. |
| 7,569,232 B2 | 8/2009 | Man et al. |
| 7,569,528 B2 | 8/2009 | Lant et al. |
| 7,598,218 B2 | 10/2009 | Stolte et al. |
| 7,601,789 B2 | 10/2009 | Morris et al. |
| 7,618,545 B2 | 11/2009 | Wakao et al. |
| 7,682,403 B2 | 3/2010 | Gohl et al. |
| 7,686,892 B2 | 3/2010 | Smets et al. |
| 7,723,083 B2 | 5/2010 | DiCosimo et al. |
| 7,771,737 B2 | 8/2010 | Man et al. |
| 7,863,234 B2 | 1/2011 | Maki et al. |
| 7,875,720 B2 | 1/2011 | Morris et al. |
| 7,887,641 B2 | 2/2011 | Man et al. |
| 7,910,371 B2 | 3/2011 | Johnson |
| 7,915,445 B2 | 3/2011 | Maatta et al. |
| 7,919,122 B2 | 4/2011 | Okano et al. |
| 7,922,828 B2 | 4/2011 | Smith et al. |
| 7,949,432 B2 | 5/2011 | Rice |
| 7,981,679 B2 | 7/2011 | Rice |
| 7,985,318 B2 | 7/2011 | Shevchenko et al. |
| 8,017,409 B2 | 9/2011 | Tokhtuev et al. |
| 8,030,351 B2 | 10/2011 | Gutzmann et al. |
| 8,071,528 B2 | 12/2011 | Smith et al. |
| 8,080,404 B1 | 12/2011 | Turetsky et al. |
| 8,084,756 B2 | 12/2011 | Tokhtuev et al. |
| 8,110,603 B2 | 2/2012 | Kawabata et al. |
| 8,119,412 B2 | 2/2012 | Kraus |
| 8,153,573 B2 | 4/2012 | Miralles et al. |
| 8,178,336 B2 | 5/2012 | Derkx et al. |
| 8,226,939 B2 | 7/2012 | Herdt et al. |
| 8,231,917 B2 | 7/2012 | Herdt et al. |
| 8,236,573 B2 | 8/2012 | Tokhtuev et al. |
| 8,241,624 B2 | 8/2012 | Herdt et al. |
| 8,309,507 B2 | 11/2012 | Fernandez Prieto et al. |
| 8,344,026 B2 | 1/2013 | Li et al. |
| 8,426,634 B2 | 4/2013 | Neas et al. |
| 8,729,296 B2 | 5/2014 | Fast et al. |
| 8,822,719 B1 * | 9/2014 | Li .................. A01N 37/02 |
| | | 562/2 |
| 9,005,669 B2 | 4/2015 | Allen et al. |
| 9,012,504 B2 | 4/2015 | Olson et al. |
| 9,034,390 B2 | 5/2015 | Kielbania, Jr. |
| 9,288,992 B2 * | 3/2016 | Li .................. A01N 25/22 |
| 9,321,664 B2 * | 4/2016 | Li .................. C11D 3/394 |
| 9,585,397 B2 * | 3/2017 | Li .................. A01N 37/02 |
| 9,676,711 B2 | 6/2017 | Junzhong et al. |
| 9,752,105 B2 | 9/2017 | Stokes et al. |
| 2001/0054201 A1 | 12/2001 | Wang et al. |
| 2002/0007516 A1 | 1/2002 | Wang |
| 2002/0055043 A1 | 5/2002 | Morikawa et al. |
| 2002/0064565 A1 | 5/2002 | Karagoezian |
| 2002/0157189 A1 | 10/2002 | Wang et al. |
| 2002/0161258 A1 | 10/2002 | Miracle et al. |
| 2002/0188026 A1 | 12/2002 | Singh et al. |
| 2003/0045443 A1 | 3/2003 | Korber et al. |
| 2003/0100468 A1 | 5/2003 | Smerznak et al. |
| 2003/0100469 A1 | 5/2003 | Connor et al. |
| 2003/0148909 A1 | 8/2003 | Del Duca et al. |
| 2003/0154556 A1 | 8/2003 | Del Duca et al. |
| 2003/0234382 A1 | 12/2003 | Sato et al. |
| 2003/0235623 A1 | 12/2003 | Van Oosterom |
| 2004/0002616 A1 | 1/2004 | Preto et al. |
| 2004/0010858 A1 | 1/2004 | Detering et al. |
| 2004/0016060 A1 | 1/2004 | Detering et al. |
| 2004/0025262 A1 | 2/2004 | Hamers et al. |
| 2004/0033269 A1 | 2/2004 | Hei et al. |
| 2004/0035537 A1 | 2/2004 | Delmas et al. |
| 2004/0072718 A1 | 4/2004 | Price et al. |
| 2004/0077514 A1 | 4/2004 | Price et al. |
| 2004/0107506 A1 | 6/2004 | Detering et al. |
| 2004/0139559 A1 | 7/2004 | Detering et al. |
| 2004/0266653 A1 | 12/2004 | Delplancke et al. |
| 2005/0000908 A1 | 1/2005 | Karlsson et al. |
| 2005/0008526 A1 | 1/2005 | Bianchetti et al. |
| 2005/0222003 A1 | 10/2005 | Gagliardi et al. |
| 2005/0226800 A1 | 10/2005 | Wang et al. |
| 2005/0281773 A1 | 12/2005 | Wieland et al. |
| 2006/0040847 A1 | 2/2006 | Weibel |
| 2006/0088498 A1 | 4/2006 | Martin et al. |
| 2006/0172909 A1 | 8/2006 | Schmiedel et al. |
| 2006/0173209 A1 | 8/2006 | Vineyard et al. |
| 2006/0199742 A1 | 9/2006 | Arisz et al. |
| 2006/0254001 A1 | 11/2006 | Hoeffkes et al. |
| 2006/0257964 A1 | 11/2006 | Larose |
| 2006/0276366 A1 | 12/2006 | Deljosevic et al. |
| 2007/0010420 A1 | 1/2007 | Lange et al. |
| 2007/0042924 A1 | 2/2007 | DiCosimo et al. |
| 2007/0087954 A1 | 4/2007 | Wang et al. |
| 2007/0093407 A1 | 4/2007 | Bianchetti et al. |
| 2007/0102359 A1 | 5/2007 | Lombardi et al. |
| 2007/0113875 A1 | 5/2007 | Wang et al. |
| 2007/0163779 A1 | 7/2007 | Rae et al. |
| 2007/0173430 A1 | 7/2007 | Sauter et al. |
| 2007/0281002 A1 | 12/2007 | Morales et al. |
| 2008/0064619 A1 | 3/2008 | Bastigkeit et al. |
| 2008/0095861 A1 | 4/2008 | Walker |
| 2008/0146482 A1 | 6/2008 | Schneiderman et al. |
| 2008/0176784 A1 | 7/2008 | Clowes et al. |
| 2008/0194449 A1 | 8/2008 | Becker et al. |
| 2008/0312107 A1 | 12/2008 | Harris et al. |
| 2009/0005286 A1 | 1/2009 | Detering et al. |
| 2009/0011971 A1 | 1/2009 | Evers |
| 2009/0018049 A1 | 1/2009 | Stolte et al. |
| 2009/0047176 A1 | 2/2009 | Cregger et al. |
| 2009/0061017 A1 | 3/2009 | Pedersen et al. |
| 2009/0075856 A1 | 3/2009 | Schmiedel et al. |
| 2009/0088347 A1 | 4/2009 | Mukhopadhyay et al. |
| 2009/0148686 A1 | 6/2009 | Urankar et al. |
| 2009/0175956 A1 | 7/2009 | Buschmann et al. |
| 2009/0188055 A1 | 7/2009 | Bernhardt et al. |
| 2009/0221704 A1 | 9/2009 | Aksela et al. |
| 2009/0249557 A1 | 10/2009 | Maki et al. |
| 2009/0269324 A1 | 10/2009 | Herdt et al. |
| 2009/0294382 A1 | 12/2009 | Fukuyo et al. |
| 2010/0021557 A1 | 1/2010 | Li et al. |
| 2010/0021558 A1 | 1/2010 | Dada et al. |
| 2010/0041579 A1 | 2/2010 | Bianchetti et al. |
| 2010/0048730 A1 | 2/2010 | Li et al. |
| 2010/0084603 A1 | 4/2010 | Narayan et al. |
| 2010/0108566 A1 | 5/2010 | Scattergood et al. |
| 2010/0140186 A1 | 6/2010 | Huang et al. |
| 2010/0160449 A1 | 6/2010 | Rovison, Jr. et al. |
| 2010/0222242 A1 | 9/2010 | Huang et al. |
| 2010/0227000 A1 | 9/2010 | Ames et al. |
| 2010/0286017 A1 | 11/2010 | Righetto |
| 2010/0308260 A1 | 12/2010 | Maki et al. |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |
| 2011/0217761 A1 | 9/2011 | Hilgren et al. |
| 2011/0240510 A1 | 10/2011 | De Poortere et al. |
| 2011/0257060 A1 | 10/2011 | Dykstra |
| 2012/0012307 A1 | 1/2012 | Nevin |
| 2012/0024525 A1 | 2/2012 | Svarczkopf et al. |

(56) References Cited

U.S. PATENT DOCUMENTS

| | | |
|---|---|---|
| 2012/0052134 A1 | 3/2012 | Li et al. |
| 2012/0070339 A1 | 3/2012 | Lawal |
| 2012/0085236 A1 | 4/2012 | McCorriston et al. |
| 2012/0085931 A1 | 4/2012 | Burns et al. |
| 2012/0097614 A1 | 4/2012 | Silva et al. |
| 2012/0149121 A1 | 6/2012 | Tokhtuev et al. |
| 2012/0164236 A1 | 6/2012 | Iwasa et al. |
| 2012/0172441 A1 | 7/2012 | Li et al. |
| 2012/0225943 A1 | 9/2012 | Gohl et al. |
| 2012/0321510 A1 | 12/2012 | Herdt et al. |
| 2013/0018097 A1 | 1/2013 | Bolduc et al. |
| 2013/0022496 A1 | 1/2013 | Herdt et al. |
| 2013/0247308 A1 | 9/2013 | Duerrschmidt et al. |
| 2014/0096971 A1 | 4/2014 | Keizer et al. |
| 2014/0097144 A1 | 4/2014 | Li et al. |
| 2014/0120179 A1 | 5/2014 | Smith et al. |
| 2014/0121272 A1 | 5/2014 | Smith et al. |
| 2014/0255514 A1 * | 9/2014 | Li ............... A01N 37/16 424/682 |
| 2014/0335199 A1 * | 11/2014 | Li ............... A01N 37/02 424/616 |
| 2016/0200595 A1 * | 7/2016 | Li ............... C11D 3/394 210/759 |
| 2017/0020130 A1 | 1/2017 | Buschmann et al. |

FOREIGN PATENT DOCUMENTS

| | | |
|---|---|---|
| CN | 1020197 | 3/1993 |
| CN | 1092385 A | 12/1993 |
| CN | 1117298 A | 10/1995 |
| CN | 1162132 A | 10/1996 |
| CN | 1231599 A | 10/1999 |
| CN | 1751768 A | 3/2006 |
| CN | 100486668 C | 5/2009 |
| CN | 102066240 A | 5/2011 |
| CN | 102105443 A | 6/2011 |
| CN | 102256484 A | 11/2011 |
| CN | 104703926 B | 12/2016 |
| DE | 1024514 | 2/1958 |
| DE | 19754290 A1 | 6/1999 |
| DE | 19853845 A1 | 5/2000 |
| DE | 10011273 A1 | 9/2001 |
| EP | 0061393 A1 | 9/1982 |
| EP | 0068547 A1 | 1/1983 |
| EP | 0075419 A2 | 3/1983 |
| EP | 0122041 A2 | 10/1984 |
| EP | 0231632 A2 | 8/1987 |
| EP | 0233730 A2 | 8/1987 |
| EP | 0267047 A2 | 5/1988 |
| EP | 0273775 A2 | 7/1988 |
| EP | 0349220 A2 | 1/1990 |
| EP | 0384911 A2 | 8/1990 |
| EP | 0387049 A2 | 9/1990 |
| EP | 0395902 A2 | 11/1990 |
| EP | 0396341 A2 | 11/1990 |
| EP | 0442549 B1 | 8/1991 |
| EP | 0280697 B1 | 9/1992 |
| EP | 0626371 A1 | 11/1994 |
| EP | 0741776 B1 | 11/1996 |
| EP | 0751210 A1 | 1/1997 |
| EP | 0751933 B1 | 8/1997 |
| EP | 0845526 A2 | 6/1998 |
| EP | 0906950 A1 | 4/1999 |
| EP | 1001012 A1 | 5/2000 |
| EP | 1010749 A2 | 6/2000 |
| EP | 1099750 A2 | 5/2001 |
| EP | 1247802 A1 | 10/2002 |
| EP | 1114137 B1 | 7/2004 |
| EP | 1129171 B1 | 8/2005 |
| EP | 1717302 A1 | 4/2008 |
| EP | 1931628 B1 | 6/2008 |
| EP | 1328616 A2 | 7/2008 |
| EP | 1926808 B1 | 7/2011 |
| EP | 2271410 B1 | 10/2011 |
| EP | 2522714 A1 | 11/2012 |
| EP | 2522715 A1 | 11/2012 |
| EP | 2471941 B1 | 9/2015 |
| EP | 2714877 B1 | 7/2017 |
| EP | 2566943 B1 | 9/2017 |
| GB | 1041417 | 9/1966 |
| GB | 1198734 | 7/1970 |
| GB | 1584170 | 2/1981 |
| GB | 2172897 A | 10/1986 |
| GB | 2177716 A | 1/1987 |
| GB | 2178754 A | 2/1987 |
| GB | 2179364 A | 3/1987 |
| GB | 2179365 A | 3/1987 |
| GB | 2187199 A | 9/1987 |
| GB | 2195124 A | 3/1988 |
| GB | 2195125 A | 3/1988 |
| GB | 2208233 A | 3/1988 |
| GB | 2195649 A | 4/1988 |
| GB | 2279660 A | 1/1995 |
| GB | 2281744 A | 3/1995 |
| GB | 2361687 A | 10/2000 |
| JP | 59206495 A | 11/1984 |
| JP | 60230000 A | 11/1985 |
| JP | 62155203 A | 7/1987 |
| JP | 63165364 A | 7/1988 |
| JP | 01297499 A | 11/1989 |
| JP | 02049765 A | 2/1990 |
| JP | 3119174 A | 5/1991 |
| JP | 5503507 A | 6/1993 |
| JP | 5186989 A | 7/1993 |
| JP | 5507951 A | 11/1993 |
| JP | 6100531 A | 4/1994 |
| JP | 6503372 | 4/1994 |
| JP | 3305920 A | 11/1994 |
| JP | 6510526 | 11/1994 |
| JP | 892595 A | 4/1996 |
| JP | 8092594 A | 4/1996 |
| JP | 8143898 A | 6/1996 |
| JP | 8245549 A | 9/1996 |
| JP | 2000505136 A | 4/2000 |
| JP | 2000357633 A | 12/2000 |
| JP | 2002105352 A | 4/2002 |
| JP | 200645146 A | 2/2006 |
| JP | 200645147 A | 2/2006 |
| JP | 2006045147 A | 2/2006 |
| JP | 200784589 A | 4/2007 |
| JP | 2007520479 A | 7/2007 |
| JP | 2007523892 A | 8/2007 |
| JP | 2009500415 A | 1/2009 |
| JP | 2011518775 A | 6/2011 |
| JP | 2012126740 A | 7/2012 |
| JP | 2012126741 A | 7/2012 |
| JP | 2012126918 A | 7/2012 |
| JP | 2012149080 A | 8/2012 |
| NZ | 587218 A | 4/2012 |
| WO | 9007501 A1 | 7/1990 |
| WO | 9107375 A1 | 5/1991 |
| WO | 199113058 A1 | 9/1991 |
| WO | 91151 A1 | 10/1991 |
| WO | 9114674 A2 | 10/1991 |
| WO | 9115474 A1 | 10/1991 |
| WO | 9403395 A1 | 2/1994 |
| WO | 9403580 A1 | 2/1994 |
| WO | 199410284 A1 | 5/1994 |
| WO | 9413776 A1 | 6/1994 |
| WO | 9418299 A1 | 8/1994 |
| WO | 9419446 A1 | 9/1994 |
| WO | 9424869 A1 | 11/1994 |
| WO | 9429509 A1 | 12/1994 |
| WO | 9502030 A1 | 1/1995 |
| WO | 9504128 A1 | 2/1995 |
| WO | 9521122 A1 | 8/1995 |
| WO | 9521290 A1 | 8/1995 |
| WO | 9528471 A1 | 10/1995 |
| WO | 9528472 A1 | 10/1995 |
| WO | 9531527 A1 | 11/1995 |
| WO | 9533816 A1 | 12/1995 |
| WO | 9534269 A1 | 12/1995 |
| WO | 199533816 A1 | 12/1995 |

(56) References Cited

FOREIGN PATENT DOCUMENTS

| | | |
|---|---|---|
| WO | 9610072 A1 | 4/1996 |
| WO | 9614384 A1 | 5/1996 |
| WO | 9616148 A1 | 5/1996 |
| WO | 9633254 A1 | 10/1996 |
| WO | 9700938 A1 | 1/1997 |
| WO | 9732871 A1 | 9/1997 |
| WO | 9742286 A1 | 11/1997 |
| WO | 9743393 A2 | 11/1997 |
| WO | 9800528 A1 | 1/1998 |
| WO | 9803513 A1 | 1/1998 |
| WO | 9804659 A3 | 2/1998 |
| WO | 9805749 A1 | 2/1998 |
| WO | 9811189 A1 | 3/1998 |
| WO | 9811777 A1 | 3/1998 |
| WO | 9818893 A1 | 5/1998 |
| WO | 9820116 A1 | 5/1998 |
| WO | 9919451 A1 | 4/1999 |
| WO | 9931215 A1 | 6/1999 |
| WO | 9932598 A1 | 7/1999 |
| WO | 9964556 A1 | 12/1999 |
| WO | 0042145 A1 | 7/2000 |
| WO | 0042158 A1 | 7/2000 |
| WO | 0070951 A1 | 11/2000 |
| WO | 0076963 A1 | 12/2000 |
| WO | 0078911 A1 | 12/2000 |
| WO | 0119414 A1 | 3/2001 |
| WO | 200144176 A1 | 6/2001 |
| WO | 200170030 A2 | 9/2001 |
| WO | 0187358 A1 | 11/2001 |
| WO | 0208076 A2 | 1/2002 |
| WO | 02088076 A1 | 11/2002 |
| WO | 03006581 A2 | 1/2003 |
| WO | 2003050343 A2 | 6/2003 |
| WO | 03067989 A1 | 8/2003 |
| WO | 2003085818 A1 | 10/2003 |
| WO | 2004033269 A2 | 4/2004 |
| WO | 2004044266 A1 | 5/2004 |
| WO | 2005109981 A1 | 11/2005 |
| WO | 2006016145 A1 | 2/2006 |
| WO | 2006094232 A1 | 9/2006 |
| WO | 2006118594 A2 | 11/2006 |
| WO | 2006131503 A2 | 12/2006 |
| WO | 2007008478 A1 | 1/2007 |
| WO | 2007013324 A1 | 2/2007 |
| WO | 2007066302 A2 | 6/2007 |
| WO | 2008005058 A1 | 1/2008 |
| WO | 2009023492 A2 | 2/2009 |
| WO | 2009040769 A1 | 4/2009 |
| WO | 2009053686 A1 | 4/2009 |
| WO | 2009118714 A2 | 10/2009 |
| WO | 2009141548 A2 | 11/2009 |
| WO | 2010050634 A1 | 5/2010 |
| WO | 2010080274 A2 | 7/2010 |
| WO | 2010090125 A1 | 8/2010 |
| WO | 200100765 A1 | 1/2011 |
| WO | 2011083295 A1 | 7/2011 |
| WO | 2011089313 A2 | 7/2011 |
| WO | 2011146557 A1 | 11/2011 |
| WO | 2011159859 A2 | 12/2011 |
| WO | 2012090124 A1 | 6/2012 |
| WO | 2012090124 A2 | 7/2012 |

OTHER PUBLICATIONS

Tsunokawa, Youko, "A Versatile Method for Preparation of O-Alkylperosycarbonic Acids: Epoxidation wtih Alkyloxycarbonlimidazoles and Hydrogen Peroxide", Tetrahedron Letters, vol. 23, No. 20, (Jan. 1, 1982), pp. 2113-2116, Jan. 1, 1982
Swern, Daniel, "Organic Peroxides", Wiley-Interscience, vol. 1, (1970), 8 pages, Jan. 1, 1970.
Suchy, Miro, et al, 1998 Pulping Conference, "Improving Alkaline Peroxide Delignification Using a Vanadium Activiator", Book 3, 15 pages, Oct. 25, 1998.
Korean Intellectual Property Office, PCT/US2013/063512, filed Oct. 4, 2013, "The International Search Report", dated Dec. 26, 2013, 10 pages, Dec. 26, 2013.
Klaas, Mark Rusch gen., Lipase-catalyzed conversions of trimethylsilyl ethers: deprotection, acetylation, epoxidation and one-pot multi-step reactions, pp. 283-505, Feb. 26, 1999.
Klaas, Mark Rusch gen., "Lipase-catalyzed conversions of trimethylsilyl ethers: deprotection, acetylation, epoxidation and one-pot-multi-step reactions", 7 pages, Feb. 26, 1999.
Klaas, Mark Rusch gen., "Bioclatalyic peroxy acide formation for disinfection", pp. 499-505, May 16, 2002.
Rizkalla, E.N., et al, "Metal Chelates of Phosphonate-Containing Ligands", Talanta, vol. 27, pp. 715-719, Mar. 7, 1980.
United Nations, "Recommendations on the Transport of Dangerous Goods", 17th Rev. Ed., vol. 1, (Jan. 1, 2011), 440 pages, Jan. 31, 2011.
Popov, Konstantin, "Critical Evaluation of Stability Constants of Phosphonic Acids", Pure Applied Chemistry, (2001) vol. 73, No. 10, pp. 1641-1677, Dec. 31, 2001.
Korean Patent Office, "The International Search Report", issued in connection to International Applicaiton No. PCT/US2014/017283, dated Apr. 28, 2014, 19 pages, Apr. 28, 2014.
Ogata, Y., et al, "The Formation of Peracids by the Perhydrolysis with Alkaline Hydrogen Peroxide", Tetrahedron, vol. 23, pp. 3327-3332, Dec. 13, 1996.
Ogata, Shin, et al, Radical Scavenging Activities of Niacin-Related Compounds, KBA, (2002), vol. 66, pp. 641-645, Nov. 2, 2001.
Nowack, Bernd, "Environmental chemistry of phosphates", Water Research, (Jan. 31, 2003), pp. 1-7, Jan. 31, 2003.
Muurinene, Esa, "Organosols Pulping", dissertation presented to the faculty of technology, University of Oulu, Finland, (Jun. 30, 2000) 314 pages, Jun. 30, 2000.
Malow, M. et al, "Prediction of the self-accelerating decomposition temperature (SADT) for liquid organic peroxides from differential scanning calorimetry (DSC) measurements", Journal of Hazardous Materials, vol. A120 (2005), pp. 21-24, Dec. 16, 2004.
Hatsuo, Maeda, "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide", vol. 50, pp. 169-174, Feb. 28, 2002.
United States Patent and Trademark Office, "Non-final Office Action", issued in connection to U.S. Appl. No. 13/785,405, dated Oct. 22, 2013, 14 pages, Oct. 22, 2103.
Leveneur, Sebastien, "Synthesis of peroxypropionic acid from propionic acid and hydrogen peroxide over heterogeneous catalysts", vol. 147, pp. 323-329, Nov. 20, 2008.
Leistner, L., "Principles and applications for hurdle technology", G.W. Gould, 1995, pp. 1-21, Jan. 1, 1995.
Leistner, Lothar, "Basic aspects of good preservation by hurdle technology", International Journal of Food Microbiology, vol. 55, pp. 181-186, Dec. 30, 2000.
Lee, Jin Jung, "Hydrolytic stability of a series of lactam-based cationic bleach activators and their impact on cellulose peroxide bleaching", Cellulose, (2010), pp. 671-678, Dec. 8, 2009.
Industry Week, "Report: Fracking to Grow U.S. Frack Water-Treatment Market Nine-Fold by 2020", Industry Week, (2012), 2 pages, last accessed on Jun. 7, 2013 at 1:55 P.M, Jan. 5, 2012.
Effkemann, Stefan et al, "Peroxide analysis in laundry detergents using liquid chromatography", Analytica Chimica Acta, pp. 97-103, Jan. 2, 1998.
Dannacher, Josepf J., "Catalytic bleach: Most valuable applicatons for smart oxidation chemistry", Journal of Molecular Catalysis, vol. 251, pp. 159-176, Mar. 20, 2006.
Chung, L., "Coordinative Binding of Divalent Cations with Ligands Related to Bacterial Spores", Biophysical Journal, vol. 11, pp. 1-14, Dec. 30, 1971.
Carboni-Oerlemans, Chiara, "Hydrolase-catalysed synthesis of peroxycarboxylic acids: Biocatalytic promiscuity for practical applications", JRL of Biotech., vol. 126, (Apr. 7, 2006), pp. 140-151, Apr. 7, 2006.

(56) References Cited

OTHER PUBLICATIONS

Brooks, Robert et al, Alkaline hydrogen peroxide bleaching of cellulose, Cellulose, vol. 7, No. 3 (Sep. 30, 2000), 26 pgs. Sep. 30, 2000.
Helrich, Kenneth, AOAC, "Agricultural Chemicals; Contaminants; Drugs", 15th Ed., (1990), vol. 1, 11 pages, Jan. 1, 1990.
United States Patent and Trademark Office, "Non-final Office Action", issued in connection with U.S. Appl. No. 13/844,515, dated Dec. 5, 2014, 11 pages, Dec. 5, 2014.
State Intellectual Property Office of the People's Republic of China, "Non-final Office Action", issued in connection with Chinese Application No. 210380051957.2, dated Nov. 24, 2015, 32 pages, Nov. 24, 2015.
State Intellectual Property Office of the People's Republic of China, "Non-final Office Action", issued in connection to Chines Application No. 201380014182.1, dated Jun. 18, 2015, 26 pages, Jun. 18, 2015.
IP Australia, "Patent Examination Report No. 2", issued in connection with AU Application Serial No. 2012201804, 3 pages, (2013), Jul. 1, 2013.
IP Australia, "Patent Examination Report No. 1", issued in connection with AU Application Serial No. 2012201804, 3 pages, (2013), Mar. 27, 2013.
IP Australia, "Patent Examination Report No. 2", issued in connection with AU Application Serial No. 2012201802, (2013), 3 pages, Mar. 5, 2013.
IP Australia, "Patent Examinination Report No. 2", issued in connection with AU Application Serial No. 2012201800, (2013), 3 pages, Jul. 3, 2013.
IP Australia, "Patent Examination Report No. 1", issued in connection with AU Application Serial No. 2012201800, (2013), 3 pages, Feb. 27, 2013.
IP Australia, "Patent Examination Report No. 2", issued in connection with AU Application Serial No. 2009230713, (2013), 3 pages, Jul. 1, 2013.
IP Australia, "Patent Examination Report No. 1", issued in connection with AU Application Serial No. 2009230713, (2013), 3 pages, Feb. 22, 2013.
Examination Report No. 1 for AU 2013326904, dated Jul. 4, 2017, 5 pages.
Response to Communication pursuant to Article 94(3) EPC for EP 13 844 411.2 dated May 31, 2017, 21 pages.
Response to Communication pursuant to Article 94(3) EPC for EP 15 184 379.4, dated May 31, 2017, 25 pages.
A.O.A.C. "Use Dilution Methods," Official Methods of Analysis of the Association of Official Analytical Chemists, paragraphs 955.14 and applicable sections, 15th Edition, (1990).
Chen, J., "Enhanced Alkaline Peroxide Bleaching of Softwood Kraft Pulps Using a New Activator," Journal of Pulp and Paper Science: vol. 27, No. 12, 4 pages, (2001).
ECOLAB USA Inc., et al., PCT/IB2011/055830, filed Dec. 20, 2011, "Notification of Transmittal of the International Search Report and the Written Opinion of the International Searching Authority, or the Declaration," 8 pages, dated Aug. 24, 2012.
ECOLAB USA Inc., et al., PCT/IB2011/055832, "Notification of Transmittal of the International Search Report and the Written Opinion of the International Searching Authority, or the Declaration," 14 pages, dated Aug. 14, 2012.
Germicidal and Detergent Sanitizing Action of Disinfectants, Official Methods of Analysis of the Association of Official Analytical Chemists, paragraph 960.09 and applicable sections, 15th Edition, EPA Guideline 91-2), (1990).
"Recommendations on the Transport of Dangerous Goods, Manual of Tests and Criteria", 5th revised edition, UN, sect. 28.4.4, p. 314, (2009).
Tsunokawa, Youko et al., "A Versatile Method for Preparation of O-Alkylperoxycarbonic Acids: Epoxidation with Alkyloxycarbonylimidazoles and Hydrogen Peroxide," Tetrahedron Letters, vol. 23, No. 20, pp. 2113-2116, (1982).
Yin, De Lu (Tyler), et al., "Switching Catalysis from Hydrolysis to Perhydrolysis in Pseudomonas fluorescense Esterase," Biochemistry 49:1931-1942, Jan. 29, 2010.
ECOLAB USA Inc., PCT/US2013/030904, "International Search Report and Written Opinion of the International Searching Authority," 14 pages, dated Jul. 5, 2013.
Database CAPLUS Chemical Abstracts Service, Accession No. 1960:97225, abstract of DE 1024514, "Oxidation of Organic Compounds with Hydrogen Peroxide in the Liquid Base," Feb. 20, 1958.
ECOLAB USA Inc., PCT/US2013/063512, "International Search Report and Written Opinion of the International Searching Authority," 10 pages, dated Dec. 26, 2013.
ECOLAB USA Inc., Supplementary European Search Report for EP 13844411.2, 7 pages, dated Jan. 19, 2016.
ECOLAB USA Inc., Supplementary European Search Report for EP 15184379.4, 7 pages, dated Jan. 19, 2016.

* cited by examiner

EFFICIENT STABILIZER IN CONTROLLING SELF ACCELERATED DECOMPOSITION TEMPERATURE OF PEROXYCARBOXYLIC ACID COMPOSITIONS WITH MINERAL ACIDS

CROSS-REFERENCE TO RELATED APPLICATIONS

This application is a continuation of U.S. Ser. No. 14/584,148 filed Dec. 29, 2014, which is a continuation of U.S. Ser. No. 13/785,044 filed Mar. 5, 2013, and are hereby incorporated by reference in their entirety. The entire contents of these patent applications are hereby expressly incorporated herein by reference including, without limitation, the specification, claims, and abstract, as well as any figures, tables, or drawings thereof.

This application is also related to U.S. application Ser. No. 13/785,047 titled "A Defoamer Useful In A Peracid Composition With Anionic Surfactants" and Ser. No. 13/785,405 titled "Peroxycarboxylic Acid Compositions Suitable For Inline Optical Or Conductivity Monitoring," without a claim of priority. The entire contents of these patent applications are hereby expressly incorporated herein by reference including, without limitation, the specification, claims, and abstract, as well as any figures, tables, or drawings thereof.

FIELD OF THE INVENTION

The invention relates to peroxycarboxylic acid compositions that are liable to exothermic decomposition which are stabilized under highly acidic conditions (e.g. high mineral acid levels) to provide improved transport and/or storage according to the invention. The compositions are also low odor and low/no VOC dual functioning acid wash and sanitizing peroxycarboxylic acid compositions. Still further, the stabilized compositions have improved antimicrobial efficacy in comparison to conventional mixed peroxycarboxylic acid compositions for sanitizing applications, while providing these additional benefits of improved safety for transport and/or storage.

BACKGROUND OF THE INVENTION

Peroxycarboxylic acids (i.e. peracids, such as peracetic acid) fall into the chemical category of "organic peroxides" which in turn are classified as self-reactive, self-heating substances. Self-reactive substances are strictly regulated by the US Department of Transportation (DOT) following the guidance of the UN Committee for the Transport of Dangerous Goods (TDG). Like the US DOT most local and national governments strictly observe the UN TDG guidance thus making their "guidance" essentially a world wide requirement. These guidances may be found in the UN document known as the "orange book," titled Recommendations on the Transport Of Dangerous Goods, $5^{th}$ revised edition, 2009.

The concern about self-heating substances is that most decomposition processes accelerate as temperature rises and usually exponentially. A self-heating process producing heat faster than it can cool is the definition of a runaway reaction. In the case of organic peroxides the runaway reaction is accompanied by the generation of large volumes of gas and therefore poses an extreme explosion risk. It is therefore an absolute requirement for purposes of safety, with the ancillary benefit of improving both shelf-life and quality, that the heat generating rate of the organic peroxide containing product not exceed the cooling rate of the package. In addition, since the cooling rates decrease with increased volume, these self-heating rates limit a commercial package size which in turn limits commercial opportunities. If for example a product falls into UN category 5.2 (D), as do some organic peroxides, they may not be sold in packages with a volume greater than 50 kg. For a customer consuming hundreds of kilograms of product per day such a limitation may be unacceptable.

In summary there are two aspects (and two sets of tests) of a prospective "self-reactive substance" to address, the first involves the characterization of the chemical (5.2 A, B, C, D, E, F or G) and the second set of tests assesses the chemistry in the proposed package of commerce. By testing the chemistry in the proposed commercial package the heat loss characteristics as well as the heat generating characteristics are assessed at various "ambient" temperatures. The minimum ambient temperature at which the chemistry self heats to exceed the ambient by at least 6 degrees Celsius is defined as the "Self Accelerating Decomposition Temperature" (SADT). Restrictions on shipping, storage (i.e. refrigeration requirements) come therefore not just from the classification test but also the SADT. If for example the package has an SADT<45 degrees Celsius refrigeration is required. A requirement of refrigeration, like classification can severely restrict commercial opportunities.

Various factors impact the transportation and/or storage risk and therefore a specific product is required to be transported below its SADT. For example, the larger a container, the lower its surface-to-volume ratio will be, resulting in less transmittal of heat to the surroundings container when undergoing thermal decomposition and a reduction in the SADT. This increases the risk of storing and transporting peroxycarboxylic acid compounds susceptible to exothermic decomposition within large containers. This hazard can be minimized by storing and transporting such compositions in containers having been diluted with one or more liquids. The diluted peroxycarboxylic acids can also be formulated into suspensions, emulsions, or solutions. Aqueous emulsions or suspensions are generally considered safer formulations, because the active peroxide is dispersed in the water phase (e.g. suitable for removing heat of decomposing peroxide molecules, such as by convection and/or evaporation). Thus commercially-available peroxycarboxylic acids are usually sold in an equilibrium solution, containing the corresponding carboxylic acid to the peroxycarboxylic acid, hydrogen peroxide and water.

Storage and/or transportation containers may also be made of substances that can withstand the pressures resulting from the inevitable gaseous decay products but they must also be made of inert or semi-inert materials. For aqueous organic peroxides the most common containers are made of high density polyethylene or polypropylene fitted with vented closures. Corrosion sensitive steel for example is not used as it will contaminate the product with transition metal ions such as $Fe^{3+}$ which are catalytical decay accelerants for most organic peroxides. Packages range in size from several gram bottles to bulk storage tanks depending largely on their classification and their package-specific SADTs. Still further, peroxycarboxylic acid compositions can be transported under refrigeration.

In non-refrigeration transport and storage it becomes almost an absolute necessity to employ transition metal chelators or "stabilizers" to both elevate the SADTs as well as to maximize the shelf-life and quality of organic peroxides. These stabilizers can be used in peroxycarboxylic acid compositions to stabilize the compositions. For example, phosphonate based stabilizers, such as phosphoric acid and salts, pyrophosphoric acid and salts and 1-hydroxyethylidene-1,1-diphosphonic acid (HEDP) and salts, are the most commonly used stabilizers in peroxycarboxylic acid compositions. When used individually at a sufficient concentration, these stabilizers can significantly improve the stability of the peroxycarboxylic acid compositions, and for the conventional (i.e. non-highly acidic) peroxycarboxylic acid compositions, the stability profile achieved with these stabilizers allows for the commercial transportation and use of these compositions. However, for peroxycarboxylic acid compositions with highly acidic formulations, including for example using strong mineral acids, these stabilizers' efficacy is greatly reduced, in many instances the efficacy is essentially non-existant.

Accordingly, it is an objective of the claimed invention to develop stabilized peroxycarboxylic acid compositions having reduced storage and/or transportation hazards.

In a particular aspect, the stabilized compositions which overcome the challenges associated with the SADT of conventional peroxycarboxylic acid compositions. In addition these stabilizer compositions may even affect the DOT classification, providing in some cases an exemption from the typical UN "5.2" class for organic peracids to the reduced risk "5.1" classification.

A further object of the invention is to provide a stabilized peroxycarboxylic acid composition suitable for storage and/or transport at temperatures of at least 50° C. without presenting SADT hazards.

A still further object of the invention is to provide a stabilized, highly acidic, mixed peroxycarboxylic acid composition utilizing a unique peracid stabilizing agent.

Other objects, advantages and features of the present invention will become apparent from the following specification taken in conjunction with the accompanying drawings.

BRIEF SUMMARY OF THE INVENTION

The present invention relates to stable peroxycarboxylic acid compositions and uses thereof. An advantage of the invention is that unconventionally acidic peroxycarboxylic acid compositions, including mixed peracids, are stabilized without impacting antimicrobial and/or sanitizing efficacy of the compositions. It is an advantage of the present invention that the stabilized peroxycarboxylic acid compositions provide other benefits including low foam profile, improved material compatibility and allows for monitoring by conductivity and/or optical sensors.

In an embodiment, the present invention is directed to a composition comprising: a $C_1$-$C_{22}$ carboxylic acid; a $C_1$-$C_{22}$ percarboxylic acid; hydrogen peroxide; and a stabilizing agent, wherein the stabilizing agent is a picolinic acid or a compound having the following Formula (IA):

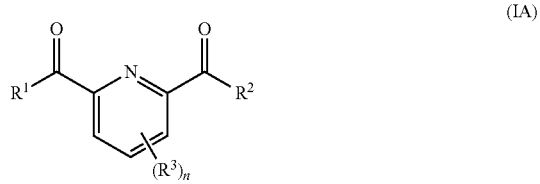

wherein $R^1$ is OH or —$NR^{1a}R^{1b}$, wherein $R^{1a}$ and $R^{1b}$ are independently hydrogen or ($C_1$-$C_6$)alkyl; $R^2$ is OH or —$NR^{2a}R^{2b}$, wherein $R^{2a}$ and $R^{2b}$ are independently hydrogen or ($C_1$-$C_6$)alkyl; each $R^3$ is independently ($C_1$-$C_6$)alkyl, ($C_2$-$C_6$)alkenyl or ($C_2$-$C_6$)alkynyl; and n is a number from zero to 3; or a salt thereof;

or a compound having the following Formula (IB):

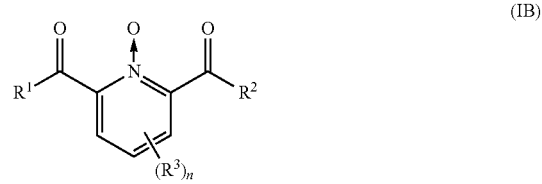

wherein $R^1$ is OH or —$NR^{1a}R^{1b}$, wherein $R^{1a}$ and $R^{1b}$ are independently hydrogen or ($C_1$-$C_6$)alkyl; $R^2$ is OH or —$NR^{2a}R^{2b}$, wherein $R^{2a}$ and $R^{2b}$ are independently hydrogen or ($C_1$-$C_6$)alkyl; each $R^3$ is independently ($C_1$-$C_6$)alkyl, ($C_2$-$C_6$)alkenyl or ($C_2$-$C_6$)alkynyl; and n is a number from zero to 3; or a salt thereof; and wherein said composition has a pH at about 3 or less.

In a further embodiment, the present invention is directed to methods of storing and/or transporting a highly acidic, stabilized peroxycarboxylic acid composition comprising: storing the above composition, wherein said composition retains at least about 80% of the C1-C22 percarboxylic acid activity after storage of about 30 days at about 50° C. In a still further aspect, the present invention is directed to a method for transporting the highly acidic, stabilized percarboxylic acid composition, preferably in bulk, wherein the SADT of said composition is elevated to at least above 45° C. during transportation and/or storage.

In a still further embodiment, the present invention is directed to methods of using highly acidic, stabilized peroxycarboxylic acid composition comprising: providing the peroxycarboxylic acid composition, contacting a surface or substrate with a use solution of the composition for sufficient time to reduce a microbial population, wherein said use solution has a pH below about 4, and wherein the composition retains at least about 80% of the $C_1$-$C_{22}$ peroxycarboxylic acid activity after storage of about 30 days at about 50° C.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
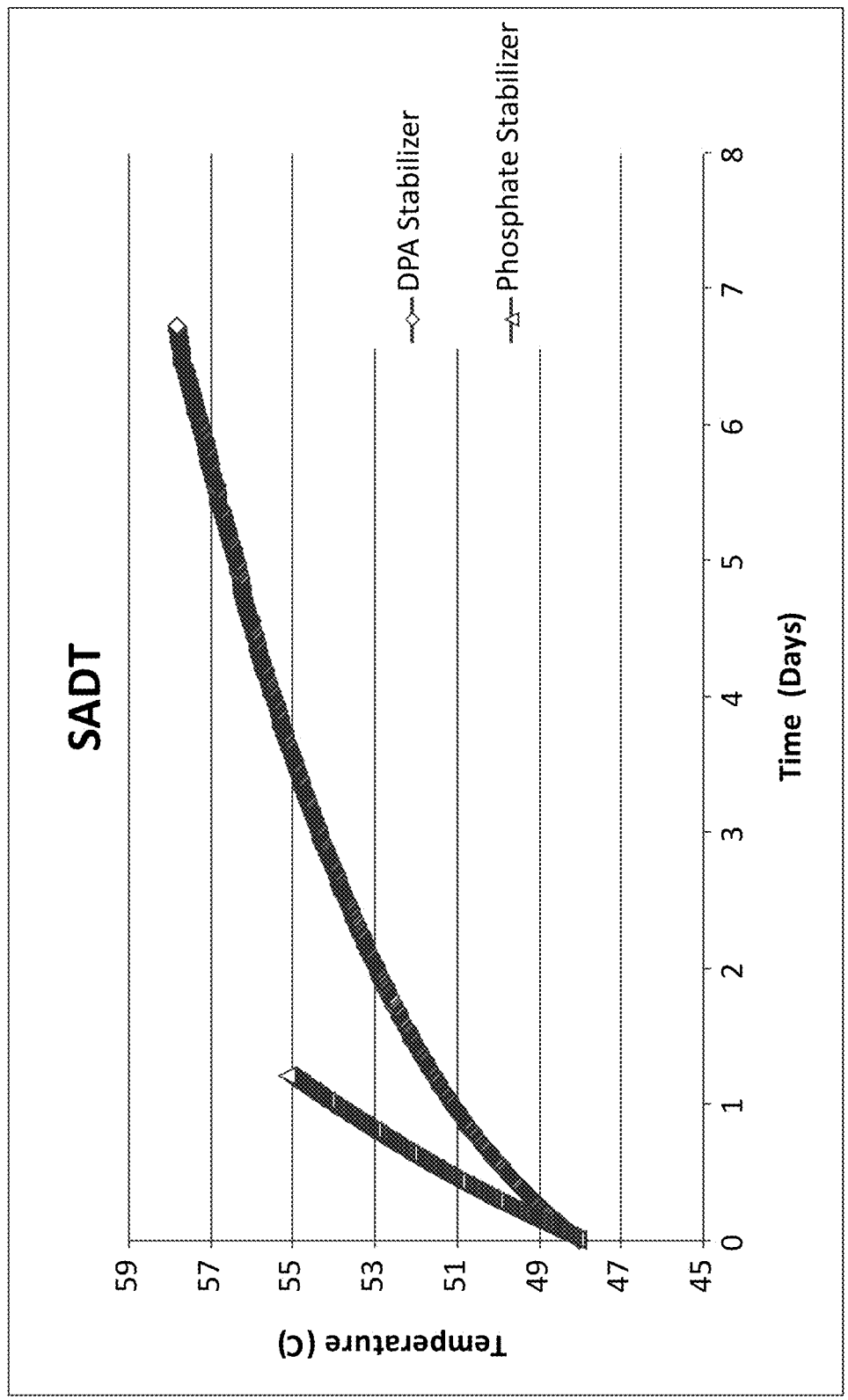
FIG. 1 shows a graph of the comparison of the SADT study of a DPA-stabilized peroxycarboxylic acid composition according to an embodiment of the invention with a phosphate based peroxycarboxylic acid composition.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular stabilized peroxycarboxylic acid compositions and methods of using the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food/plant/animal processing surfaces.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

For the purpose of this patent application, successful microbial reduction is achieved when the microbial populations are reduced by at least about 50%, or by significantly more than is achieved by a wash with water. Larger reductions in microbial population provide greater levels of protection. Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Compositions

While an understanding of the mechanism is not necessary to practice the present invention and while the present invention is not limited to any particular mechanism of action, it is contemplated that, in some embodiments, highly acidic peroxycarboxylic acid compositions are not sufficiently stabilized using conventional phosphate stabilizers. Phosphonate or other metal chelating stabilizers (e.g. HEDP/Dequest 2010) are either incompatible and/or ineffective as stabilizers with the highly acidic peracid compositions of the present invention, which results in SADT that effectively limit the transportation and/or storage of these self-accelerating decomposition compounds. The present invention provides peroxycarboxylic acid stabilizing compounds suitable for use under highly acidic, equilibrium compositions. The present invention further provides peroxycarboxylic acid stabilizing compounds suitable for use in compositions having extreme ratios of peracid to hydrogen peroxide, wherein the concentration of the peroxyacids greatly exceed the hydrogen peroxide. In an embodiment, dipicolinic acid is provided as the peroxycarboxylic acid stabilizer under strong acidic conditions in place of conventional peracid stabilizers, such as Dequest 2010 which is predominantly used in commercial peracid products. Beneficially, the peroxycarboxylic acid stabilizer under strong acidic conditions elevates the SADT of the compositions providing transportation and/or storage benefits.

According to an embodiment of the invention the stabilized peroxycarboxylic acid compositions are suitable for storage and/or transport at ambient temperatures that might occasionally reach about 50° C. In an aspect, the stabilized composition retains at least about 80% of the peroxycarboxylic acid activity after storage of about 30 days at about 50° C. Preferably, the peracid compositions retain at least about 85%, at least about 90% or greater percentage of the peracid activity after storage of about 30 days at about 50° C. According to a further embodiment, the stabilized compositions can be transported and/or stored, preferably in bulk, wherein the SADT of said composition is elevated to at least about 45° C. during transportation, or to at least about 50° C., or to at least about 60° C. (for moderate size packages) during transportation.

In an aspect, the compositions include concentrated equilibrium compositions comprising a stabilizing agent, peracid(s), hydrogen peroxide, carboxylic acid(s), a solvent, e.g., water, and optional additional functional ingredients (e.g. defoaming agents, fluorescent active compounds). In an aspect, the compositions include the exemplary ranges shown in Table 1 in weight percentage of the liquid concentrated equilibrium compositions.

TABLE 1

| Material | First Exemplary Range wt-% | Second Exemplary Range wt-% | Third Exemplary Range wt-% |
| --- | --- | --- | --- |
| Solvent (e.g. Water) | 1-75 | 10-60 | 20-40 |
| Peroxycarboxylic Acid | 0.1-40 | 1-40 | 1-20 |
| Carboxylic Acid | 0.1-90 | 1-80 | 1-50 |
| Hydrogen Peroxide | 1-90 | 1-80 | 1-50 |
| Mineral Acid | 1-50 | 1-20 | 5-20 |
| Stabilizing Agent | 0.001-25 | 0.01-10 | 0.01-1 |
| Additional Functional Ingredients (e.g. defoaming agent) | 0-25 | 0-20 | 0-10 |

In yet other aspects, the compositions according to the invention may include non-equilibrium peracid compositions, such as where a peroxycarboxylic acid is generated in situ and/or on site through a process by one or more composition (e.g. one or more part systems) comprising individual reagents combined according to the invention. In an exemplary aspect, these reagents are described herein individually along and include at least one ester of a polyhydric alcohol and a C1 to C18 carboxylic acid, an oxidizing agent, a source of alkalinity, solvents, and other functional groups/agents. An acidulant is also described herein as a reagent to be added to the compositions after the formation of the percarboxylic acid(s). Alternatively, as described herein, there may be benefits to providing the reagents in various premix formulations to decrease the number of reagents and/or increase the simplicity of the invention for generating peracid compositions for a particular use. Premix formulations suitable for use according to the invention may comprise, consist of and/or consist essentially of at least one ester of a polyhydric alcohol and a C1 to C18 carboxylic acid, an oxidizing agent, a solvent and mixtures thereof. Premix formulations suitable for use according to the invention may also comprise, consist of and/or consist essentially of at least one ester, an oxidizing agent, water, solvents, dispersing agents, surfactants, defoamers and mixtures thereof.

In some aspects the compositions, whether generated in situ or on site from one or more premix compositions or whether provided in a concentrated equilibrium composition, in a use solution have a pH at about 4 or less. Preferably, the compositions in a use solution have a pH at about 3 or less. In an aspect, the use solutions of the highly acidic, stabilized peroxycarboxylic acid compositions, when diluted pursuant to EPA sanitizer suspension preparations (e.g. dilute 1 oz. of the peracid composition to 8 Gallon with 500 ppm hard water), such that the pH of the solution is less than about 3.0, preferably between about 2.8-2.9.

Peracid Stabilizing Agent

A peracid stabilizing agent or agents are included in compositions according to the invention. Beneficially, the peracid stabilizing agent or agents prevent the decomposition of peracid in an equilibrium peracid composition. In addition, peracid stabilizing agent(s) prevent an equilibrium peracid composition from reaching their self-accelerating decomposition temperatures (SADT). The use of the peracid stabilizing agent beneficially stabilizes highly acidic equilibrium peracids including mixed peracid compositions, as well as extreme chemistries with problematic high peracid to hydrogen peroxide ratios. By elevating the SADTs of the compositions the stabilizers contribute significant safety benefits for transportation and storage of the compositions. In some aspects, the stabilizing agents delay or prevent the composition from meeting its native SADT.

In an aspect of the invention, the stabilizing agent is a pyridine carboxylic acid compound. Pyridine carboxylic acids include dipicolinic acids, including for example, 2,6-pyridinedicarboxylic acid (DPA). In a further aspect, the stabilizing agent is a picolinic acid, or a salt thereof.

In an aspect of the invention, the stabilizing agent is a picolinic acid or a compound having the following Formula (IA):

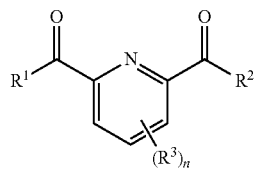

(IA)

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

In a further aspect of the invention, the peracid stabilizing agent is a compound having the following Formula (TB):

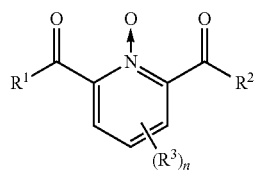

(IB)

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

In a preferred aspect, the peracid stabilizing agent is dipicolinic acid (picolinic acid, 2,6-Pyridinedicarboxylic acid) and provides stabilization for high mineral content peracids, wherein the resulting peracid composition has an elevated SADT.

Dipicolinic acid has been used as a stabilizer for peracid compositions, such as disclosed in WO 91/07375 and U.S. Pat. No. 2,609,391, which are herein incorporated by reference in their entirety. However, use of such DPA stabilizer for peracid compositions has not previously been disclosed and/or exploited for its SADT-elevating properties.

In a further aspect, the stabilizing agent may be combined with additional conventional stabilizing agents, e.g. a phosphonate based stabilizer, to beneficially provide further increase in stability of the composition, and in some aspects provide synergistic increase in SADT and peracid stability according to embodiments of the invention.

Stabilizing agents may be present in amounts sufficient to provide the intended stabilizing benefits, namely achieving the desired shelf life, and elevating the SADT of the highly acidic peroxycarboxylic acid compositions having a use solution pH of below at least 4, preferably below at least 3. As the property of the composition will vary depending upon the acidity of the particular peracid composition according to the invention, such peracid stabilizing agents may be present in a concentrated equilibrium peracid composition in amounts from about 0.001 wt-% to about 25 wt-%, 0.01 wt-% to about 10 wt-%, and more preferably from about 0.01 wt-% to about 1 wt-%. Without limiting the scope of invention, the numeric ranges are inclusive of the numbers defining the range and include each integer within the defined range.

Peracids

According to the invention, a peroxycarboxylic acid (i.e. peracid) is included for antimicrobial efficacy in the sanitizing compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Pat. No. 8,344,026, and U.S. Patent Publication Nos. 2010/0048730 and 2012/0052134, each of which are incorporated herein by reference in their entirety. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Preferably, a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like.

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

According to the invention, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, $—SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

According to the invention, aryl and heteroaryl groups can be unsubstituted or substituted on the ring by, for example, aryl, heteroaryl, alkyl, alkenyl, alkoxy, amino, carboxy, halo, nitro, cyano, $—SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic acids (e.g. C1-22) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid anhydride, carboxylic acid anhydride, sodium alcoholate or alkyl and aryl esters. Alternatively, peracids can be prepared through non-equilibrium reactions, which may be generated for use in situ, such as the methods disclosed in U.S. Patent Publication Nos. 2012/0172440 and 2012/0172441 each titled "In Situ Generation of Peroxycarboxylic Acids at Alkaline pH, and Methods of Use Thereof," which are incorporated herein by reference in their entirety. Preferably a composition of the invention includes peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with a hydroxyl group or other polar substituent such that the substituent improves the water solubility. Methods of preparing peroxyacetic acid are known to those of skill in the art including those disclosed in U.S. Pat. No. 2,833,813, which is herein incorporated herein by reference in its entirety.

In another embodiment, a sulfoperoxycarboxylic acid has the following formula:

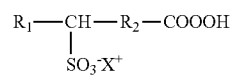

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof.

In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkylene group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group. In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In some embodiments, $R_2$ is a substituted $C_1$-$C_{10}$ alkylene group. In some embodiments, $R_2$ is a substituted $C_8$-$C_{10}$ alkylene. In some embodiments, $R_2$ is an unsubstituted $C_6$-$C_9$ alkylene. In other embodiments, $R_2$ is a $C_8$-$C_{10}$ alkylene group substituted with at least one hydroxyl group. In some embodiments, $R_2$ is a $C_{10}$ alkylene group substituted with at least two hydroxyl groups. In other embodiments, $R_2$ is a $C_8$ alkylene group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkylene.

These and other suitable sulfoperoxycarboxylic acid compounds for use in the stabilized peroxycarboxylic acid compositions of the invention are further disclosed in U.S. Pat. No. 8,344,026 and U.S. Patent Publication Nos. 2010/0048730 and 2012/0052134, which are incorporated herein by reference in its entirety.

In additional embodiments a sulfoperoxycarboxylic acid is combined with a single or mixed peroxycarboxylic acid composition, such as a sulfoperoxycarboxylic acid with peroxyacetic acid and peroxyoctanoic acid (PSOA/POOA/POAA). In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid, such as disclosed in U.S. Pat. No. 5,314,687 which is herein incorporated by reference in its entirety. In an aspect, the peracid mixture is a hydrophilic peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are employed, such as disclosed in U.S. Pat. No. 8,344,026 which is incorporated herein by reference in its entirety. Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example peracetic acid (approximately 15%) available as EnviroSan (Ecolab, Inc., St. Paul Minn.). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

In an aspect, any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ percarboxylic acid comprises peroxyacetic acid, peroxyoctanoic acid and/or peroxysulfonated oleic acid.

In an aspect of the invention, a peracid may be selected from a concentrated composition having a ratio of hydrogen peroxide to peracid from about 0:10 to about 10:0, preferably from about 0.5:10 to about 10:0.5, preferably from about 1:8 to 8:1. Various concentrated peracid compositions having the hydrogen peroxide to peracid ratios of about 0.5:10 to about 10:0.5, preferably from about 1:8 to 8:1, may be employed to produce a use solution for treatment according to the methods of the invention. In a further aspect of the invention, a peracid may have a ratio of hydrogen peroxide to peracid as low as from about 0.01 part hydrogen peroxide to about 1 part peracid. Without limiting the scope of invention, the numeric ranges are inclusive of the numbers defining the range and include each integer within the defined range.

Obtaining the preferred hydrogen peroxide to peroxycarboxylic acid ratios in a peracid composition may be obtained by a variety of methods suitable for producing a very low hydrogen peroxide to peracid ratio. In an aspect, equilibrium peracid compositions may be distilled to recover a very low hydrogen peroxide peracid mixture. In yet another aspect, catalysts for hydrogen peroxide decomposition may be combined with a peracid composition, including for example, peroxide-reducing agents and/or other biomimetic complexes. In yet another aspect, perhydrolysis of peracid precursors, such as esters (e.g. triacetin) and amides may be employed to obtain peracids with very low hydrogen peroxide. These and other methods of reducing hydrogen peroxide ratios in a peracid composition are disclosed in U.S. patent Ser. No. 13/798,311 (Ecolab 3031USU1) titled "Use of Peracetic Acid/Hydrogen Peroxide and Catalase for Treatment of Drilling Fluids, Frac Fluids, Flowback Water and Disposal Water, and Ser. Nos. 13/798,281 and 13/798,307 (3031USI1 and 3031USI2) titled "Use of Peracetic Acid/Hydrogen Peroxide and Peroxide Reducing Agents for Treatment of Drilling Fluids, Frac Fluids, Flowback Water and Disposal Water," each of which are herein incorporated by reference in their entirety.

In a preferred aspect, the $C_1$-$C_{22}$ percarboxylic acid can be used at any suitable concentration. In some embodiments, the $C_1$-$C_{22}$ percarboxylic acid has a concentration from about 0.1 wt-% to about 40 wt-% in a concentrated equilibrium composition. In other embodiments, the $C_1$-$C_{22}$ percarboxylic acid has a concentration from about 1 wt-% to about 40 wt-%, or from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. Without limiting the scope of invention, the numeric ranges are inclusive of the numbers defining the range and include each integer within the defined range.

Carboxylic Acid

The present invention includes a carboxylic acid with the peracid composition and hydrogen peroxide. A carboxylic acid includes any compound of the formula R—$(COOH)_n$, in which R can be hydrogen, alkyl, alkenyl, alkyne, acylic, alicyclic group, aryl, heteroaryl, or heterocylic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined above with respect to peracids.

Examples of suitable carboxylic acids according to the equilibrium systems of peracids according to the invention include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect of the invention, a particularly well suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid. Additional examples of suitable carboxylic acids are employed in sulfoperoxycarboxylic acid or sulfonated peracid systems, which are disclosed in U.S. Pat. No. 8,344,026, and U.S. Patent Publication Nos. 2010/0048730 and 2012/0052134, each of which are herein incorporated by reference in their entirety.

Any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic acid is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ carboxylic acid comprises acetic acid, octanoic acid and/or sulfonated oleic acid.

The $C_1$-$C_{22}$ carboxylic acid can be used at any suitable concentration. In some embodiments, the $C_1$-$C_{22}$ carboxylic acid has a concentration in an equilibrium composition from about 0.1 wt-% to about 90 wt-%. In other embodiments, the $C_1$-$C_{22}$ carboxylic acid has a concentration from about 1 wt-% to about 80 wt-%. In still other embodiments, the $C_1$-$C_{22}$ carboxylic acid has a concentration at about 1 wt-% to about 50 wt-%. Without limiting the scope of invention, the numeric ranges are inclusive of the numbers defining the range and include each integer within the defined range.

Hydrogen Peroxide

The present invention includes hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect of the invention, hydrogen peroxide is initially in an antimicrobial peracid composition in an amount effective for maintaining an equilibrium between a carboxylic acid, hydrogen peroxide, and a peracid. The amount of hydrogen peroxide should not exceed an amount that would adversely affect the antimicrobial activity of a composition of the invention. In further aspects of the invention, hydrogen peroxide concentration can be significantly reduced within an antimicrobial peracid composition. In some aspects, an advantage of minimizing the concentration of hydrogen peroxide is that antimicrobial activity of a composition of the invention is improved as compared to conventional equilibrium peracid compositions.

The hydrogen peroxide can be used at any suitable concentration. In some embodiments, a concentrated equilibrium composition has a concentration of hydrogen peroxide from about 0.5 wt-% to about 90 wt-%, or from about 1 wt-% to about 90 wt-%. In still other embodiments, the hydrogen peroxide has a concentration from about 1 wt-% to about 80 wt-%, from about 1 wt-% to about 50 wt-%. Without limiting the scope of invention, the numeric ranges are inclusive of the numbers defining the range and include each integer within the defined range.

Beneficially, the compositions and methods of the invention in providing stabilized equilibrium peracid compositions, are not reliant and/or limited according to any particular ratio of hydrogen peroxide to peracid for such enhanced stability. Instead, it is unexpected that the stabilizing agent (e.g. DPA) is suitable for providing peracid stability under high acidity/mineral acid conditions, while constraining the peracid SADT. This represents a significant improvement over the prior art, wherein DPA is an optional peracid stabilizing agent for low hydrogen peroxide containing peracid compositions. See e.g. U.S. Publication No. 2010/021558, which is herein incorporated by reference in its entirety.

Mineral Acid

In some embodiments, the present composition is a strongly acidic peracid as a result of inclusion of a strong acid. In some aspects the peracid composition has a use solution pH of 4 or less, and preferably has a use solution pH of 3 or less. In some embodiments, the present composition includes an inorganic acid. In preferred embodiments, the present composition includes a mineral acid.

Particularly suitable mineral acids include sulfuric acid ($H_2SO_4$), sodium hydrogen sulfate, nitric acid, sulfamic acid and sulfonic acids both alkyl and aryl, in particular methane sulfonic acid and dodecylbenzene, toluene, xylene, naphthalene and cumene sulfonic acid, and/or phosphoric acid ($H_3PO_4$). Additional phosphonic acids which may be used according to the invention include, for example, aminotrimethylene phosphonic acid, ethylene diamin tetramethylene phosphonic acid, hexamethylene diamin tetramethylene phosphonic acid, diethylene triamin tetramethylene phosphonic acid, and 1-hydroxyethylidene-1,1-diphosphonic acid (HEDP).

In a further aspect, the acids suitable for use include are not limited to mineral acids. Instead, acids suitable for use include strong acids, which are defined as those with a pKa near or below the lower pKas of HEDP which may cause significant protonation of the HEDP and other phosphate and phosphonate stabilizers and thus diminish their ability to stabilize the peracid chemistries. Additional description of mineral acids for use in peracid compositions is disclosed in WO 91/07375, which is herein incorporated by reference in its entirety.

In an aspect of the invention, the mineral acid providing the strong acidity of the peracid compositions can be used at any suitable concentration. In some embodiments, a concentrated equilibrium composition has a concentration of the mineral acid from about 0.5 wt-% to about 50 wt-%, or from about 1 wt-% to about 50 wt-%. In still other embodiments, the mineral acid has a concentration from about 1 wt-% to about 20 wt-%, or more preferably from about 5 wt-% to about 20 wt-%. Without limiting the scope of invention, the numeric ranges are inclusive of the numbers defining the range and include each integer within the defined range.

Additional Functional Ingredients

In some embodiments, the present composition can further comprise additional functional ingredients. In some embodiments, the highly acidic peracid composition including the stabilizing agent, mineral acid, peroxycarboxylic acid, carboxylic acid, hydrogen peroxide and water make up a large amount, or even substantially all of the total weight of the peracid compositions. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. In some aspects, the compositions may include defoaming agents, surfactants, additional antimicrobial agents, anti-redeposition agents, bleaching agents, solubility modifiers, dispersants, rinse aids, metal protecting agents, stabilizing agents, corrosion inhibitors, fragrances and/or dyes, rheology modifiers or thickeners, hydrotropes or couplers, buffers, solvents and the like.

In preferred embodiments, the compositions further include substances that aid in the solubilization of the stabilizing agent(s), including for example, hydrotropes such as sodium xylene sulfonate (SXS), sodium cumene sulfonates (SCS), surfactants, such as anionic surfactants and noinionic surfactants, and a defoaming agent. In further aspects, the composition may utilize alternative hydrotropes for solubilization of the stabilizing agent, including for example, n-octanesulfonate, a xylene sulfonate, a naphthalene sulfonate, ethylhexyl sulfate, lauryl sulfate, an amine oxide, etc.

In preferred embodiments, the compositions do not include phosphonic acid based stabilizers (e.g. pyrophosphoric acids and/or salts thereof, HEDP, $(H_{n+2}PnO_{3n+1})$).

Surfactants

In some embodiments, the compositions of the present invention include a surfactant. Surfactants suitable for use with the compositions of the present invention include, but are not limited to nonionic surfactants and/or anionic surfactants. Preferably, a low foaming anionic surfactant is included in the peroxycarboxylic acid compositions. Beneficially, according to embodiments of the invention, the use of the defoaming agent (e.g. aluminum sulfate) in combination with the surfactant overcomes the foaming issues that are known to result from the use of conventional low-foaming surfactants in peroxycarboxylic acid compositions, especially in deionized or soft water.

In some embodiments, the compositions of the present invention include about 0 wt-% to about 40 wt-% of a surfactant. In other embodiments the compositions of the present invention include about 0.1 wt-% to about 40 wt-% of a surfactant, preferably from about 0.1 wt-% to about 25 wt-% of a surfactant, and more preferably from about 1 wt-% to about 20 wt-% of a surfactant.

Anionic Surfactants

Preferably, surface active substances which are categorized as anionics because the charge on the hydrophobe is negative are utilized according to the present invention; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility. As those skilled in the art understand, anionics are excellent detersive surfactants and are therefore favored additions to heavy duty detergent compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, sulfonated fatty acids, such as sulfonated oleic acid, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R\text{—}O\text{—}(CH_2CH_2O)_n(CH_2)_m\text{—}CO_2X \quad (3)$$

in which R is a $C_8$ to $C_{22}$ alkyl group or

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

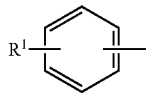

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Nonionic Surfactants

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp. Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Tetronic® compounds are tetra-flinctional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

2. Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal manufactured by Rhone-Poulenc and Triton manufactured by Union Carbide.

3. Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol™ manufactured by Shell Chemical Co. and Alfonic™ manufactured by Vista Chemical Co.

4. Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol™ manufactured by Henkel Corporation and Lipopeg™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions of the present invention containing amylase and/or lipase enzymes because of potential incompatibility.

Examples of nonionic low foaming surfactants include:

5. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

6. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

7. The alkylphenoxypolyethoxyalkanols of U.S. Pat. No. 2,903,486 issued Sep. 8, 1959 to Brown et al. and represented by the formula

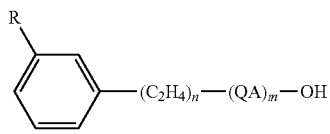

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O)_n(C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n(C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

8. Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

9. The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

10. The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

11. Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

12. Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or —$(C_2H_4O)_xH$, where x is in the range of from 1 to 3.

13. A useful class of non-ionic surfactants include the class defined as alkoxylated amines or, most particularly, alcohol alkoxylated/aminated/alkoxylated surfactants. These non-ionic surfactants may be at least in part represented by the general formulae: $R^{20}$—$(PO)_SN$-$(EO)_tH$, $R^{20}$—$(PO)_SN$-$(EO)_tH(EO)_tH$, and $R^{20}$—$N(EO)_tH$; in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}$—$(PO)_v$—$N[(EO)_wH][(EO)_zH]$ in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic™ PEA 25 Amine Alkoxylate. Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface active agents are another class of nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

14. Amine oxides are tertiary amine oxides corresponding to the general formula:

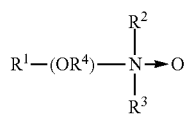

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

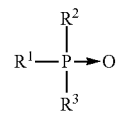

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

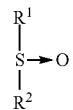

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like.

Defoaming Agent

The present invention includes a defoaming agent. Defoaming agents suitable for use in the peroxycarboxylic acid compositions according to the invention are compatible with the highly acidic peracid compositions and anionic and/or nonionic surfactants which may be employed in the peracid compositions. The defoaming agents suitable for use in the peroxycarboxylic acid compositions according to the invention, maintain a low foam profile under various water conditions, preferably under deionized or soft water conditions, and/or under mechanical action. In a still further aspect, the defoaming agents are compatible with surfactants, preferably anionic surfactants, to achieve critical performance such as coupling/wetting, improved material compatibility and enhanced biocidal efficacy. In preferred aspects, the defoaming agent provides a synergistic biocidal efficacy.

In an aspect of the invention, the defoaming agent is a metal salt, including for example, aluminum, magnesium, calcium, zinc and/or other rare earth metal salts. In a preferred aspect, the defoaming agent is a cation with high charge density, such as $Fe^{3+}$, $Al^{3+}$ and $La^{3+}$. In a preferred aspect, the defoaming agent is aluminum sulfate.

In an aspect, the defoaming agent is not a transition metal compound, which are incompatible with the highly acidic equilibrium peracid compositions according to the invention. In some embodiments, the compositions of the present invention can include antifoaming agents or defoamers which are of food grade quality given the application of the method of the invention. In a further embodiment, the compositions of the present invention can include defoaming agents which are stable in acid environments (e.g. the peracid compositions containing a mineral acid and having a use solution pH of about 4 or less) and/or are oxidatively stable.

In an aspect of the invention, the defoaming agent can be used at any suitable concentration to provide defoaming with the surfactants according to the invention and to provide synergistic biocidal efficacy. In some embodiments, a concentrated equilibrium composition has a concentration of the a defoaming agent from about 0.001 wt-% to about 10 wt-%, or from about 0.1 wt-% to about 5 wt-%. In still other embodiments, the defoaming agent has a concentration from about 0.1 wt-% to about 1 wt-%. Without limiting the scope of invention, the numeric ranges are inclusive of the numbers defining the range and include each integer within the defined range.

Fluorescent Active Compound

In an aspect, the present composition is a strongly acidic equilibrium peracid containing a fluorescent active compound that is stable in the peracid compositions according to the invention. In an aspect, the fluorescent active compound is formulated directly into the equilibrium peracid composition, instead of contained in a two or more part system (e.g. peracid precursors or preformed peracids with a fluorescent active compound added prior to use and having short stability). In additional aspects, the fluorescent active compound is further stable in and suitable for use in other peracid compositions, including compositions in concentrate and/or use solutions at both acidic and alkaline pHs. For example, in some aspects, the fluorescent active compound is further stable in highly acidic compositions (e.g. cleaning and sanitizing compositions) and caustic compositions (e.g. laundry compositions). In further aspects, the fluorescent active compound is further stable in strongly oxidant systems (often employed for sanitizing compositions), such as chlorine.

In some aspects, the fluorescent active compound may be an inert component of the composition (e.g. sanitizing compositions). In other aspects, the fluorescent active compound is an active component of the composition (e.g. cleaning compositions).

In an aspect, the fluorescent active compound is an aryl sulfonate. In other aspects, the fluorescent active compound is an alkyl aryl sulfonate. In further aspects, the fluorescent active compound is an aromatic ring with a hydrophilic group (e.g. sulfonate, carboxylic). Without being limited to a particular theory or mechanism of the invention, the inclusion of the hydrophilic group of the aromatic ring beneficially results in the compatibility of the fluorescent active compound with the peracid composition.

Exemplary suitable alkyl aryl sulfonates that can be used in the compositions as fluorescent active compounds can have an alkyl group that contains 0 to 16 carbon atoms and the aryl group can be at least one of benzene, diphenyl oxide, and/or naphthalene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include benzene sulfonate, toluene sulfonate, xylene sulfonate, cumene sulfonate, diphenyl oxide disulfonate, naphthalene sulfonate and naphthalene disulfonates, Additional exemplary suitable aromatic rings having a hydrophilic group are shown in the following formulas:

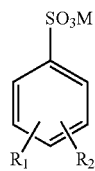 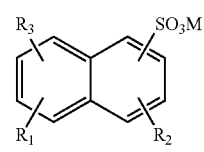

$M = H^+$, or $Na^+$
$R_1 = H$, or Alkyl
$R_2 = H$, or Alkyl $M = H^+$, or $Na^+$
$R_1 = H$, or Alkyl
$R_2 = H$, or Alkyl
$R_3 = SO_3M$, H, or Alkyl

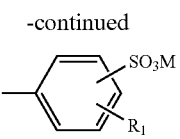

M = H⁺, or Na⁺
R₁ = H, or Alkyl
R₂ = H, or Alkyl

In an aspect, the fluorescent active compound is sodium xylene sulfonate (SXS), such as is commercially available from the Stepan Company, and/or sodium cumene sulfonate (SCS), such as is commercially available from AkzoNobel. In an aspect, the fluorescent active compound is sodium alkyl diphenyl disulfonate, such as commercially available from the Dow Company as Dowfax, such as Dowfax 2A1. In an aspect, the fluorescent active compound is sodium naphthalene sulfonate and/or disodium naphthalene disulfonate, and or alkyl naphthalene sulfonate, such as commercially available from AkzoNobel as PetroLBA.

In an aspect, the fluorescent active compound is suitable for indirect food use. In a further aspect, the fluorescent active compound is suitable for more than only visual assessment of peracid concentrations (e.g. UV light source to confirm on a dry substrate a disinfectant was applied). Instead, the fluorescent active compounds are suitable for dose quantification by optical measurement.

Additional fluorescent tracers that may have applications of use according to the invention are commercially available under the trade name TRASAR® (Nalco Company® (Naperville, Ill.)) and/or may be synthesized using techniques known to persons of ordinary skill in the art of organic chemistry.

In an aspect of the invention, fluorescent active compound can be used at any suitable concentration. In some embodiments, a concentrated equilibrium composition has a concentration of the fluorescent active compound from about 0.001 wt-% to about 10 wt-%, or from about 0.1 wt-% to about 10 wt-%. In still other embodiments, the fluorescent active compound has a concentration from about 0.5 wt-% to about 7.5 wt-%, or more preferably from about 1 wt-% to about 5 wt-%. Without limiting the scope of invention, the numeric ranges are inclusive of the numbers defining the range and include each integer within the defined range.

Methods of Delivery and Methods of Use

In an aspect, the present invention is directed to a method for storing and/or transporting a peroxycarboxylic acid composition, including storing the compositions, wherein at least about 80% of the peroxycarboxylic acid activity is retained after storage for any suitable time under any suitable conditions, e.g., retaining at least about 80% of the peroxycarboxylic acid activity after storage of about 30 days at about 50° C. Preferably, the methods include retaining at least about 85%, at least about 90%, or at least about 95% or higher of the peroxycarboxylic acid activity after storage of about 30 days at about 50° C.

In another aspect, the present invention is directed to a method for transporting a peroxycarboxylic acid containing composition, which method comprises transporting the compositions under ambient conditions wherein the SADT of the composition is at least about 45° C. during transportation. Preferably, the SADT of the composition is higher than at least about 50° C., about 55° C., about 60° C., about 65° C. or about 70° C. In a further aspect, the transporting of the peroxycarboxylic acid containing composition is in bulk e.g., 1,000 gallons and above.

In still another aspect, the present invention includes use of the compositions for sanitizing surfaces and/or products. In another aspect, the compositions of the invention are particularly suitable for use as a hard surface sanitizer and/or disinfectant, a CIP sanitizer, food and/or tissue treatment sanitizer (including direct or indirect contact sanitizer), an environmental disinfectant, a laundry bleach and disinfectant, and/or an indirect food contact sanitizer. The present methods can be used in the methods, processes or procedures described and/or claimed in U.S. Pat. Nos. 5,200,189, 5,314,687, 5,718,910, 6,165,483, 6,238,685B1, 8,017,409 and 8,236,573, each of which are herein incorporated by reference in their entirety.

The methods of use are suitable for treating a variety of surfaces, products and/or target. For example, these may include a food item or a plant item and/or at least a portion of a medium, a container, an equipment, a system or a facility for growing, holding, processing, packaging, storing, transporting, preparing, cooking or serving the food item or the plant item. The present methods can be used for treating any suitable plant item. In some embodiments, the plant item is a grain, fruit, vegetable or flower plant item, a living plant item or a harvested plant item. In addition, the present methods can be used for treating any suitable food item, e.g., an animal product, an animal carcass or an egg, a fruit item, a vegetable item, or a grain item. In still other embodiments, the food item may include a fruit, grain and/or vegetable item.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

The various methods of treatment can include the use of any suitable level of the peroxycarboxylic acid. In some embodiments, the treated target composition comprises from about 10 ppm to about 1000 ppm of the peroxycarboxylic acid, including any of the peroxycarboxylic acid compositions according to the invention.

In still another aspect, the present invention includes water treatment methods and other industrial processes uses of the compositions for sanitizing surfaces and/or products. In some aspects, the invention includes methods of using the peroxycarboxylic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid compositions are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Bio-fuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

The methods by which the peroxycarboxylic acid compositions are introduced into the aqueous fluids or liquid systems are not critical. Introduction of the peracid compositions may be carried out in a continuous or intermittent manner and will depend on the type of water and/or liquid being treated. In some embodiments, the peracid compositions are introduced into an aqueous fluid according to the methods disclosed in U.S. patent application Ser. No. 13/645,671, titled "New Method and Arrangement for Feeding Chemicals into a Hydrofracturing Process and Oil and Gas Applications", which is hereby incorporated by reference in its entirety.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

The various applications of use described herein provide the peroxycarboxylic acid compositions to a surface, liquid and/or product in need of antimicrobial and/or sanitizing treatment. Beneficially, the compositions of the invention are fast-acting. However, the present methods require a certain minimal contact time of the compositions with the surface, liquid and/or product in need of treatment for occurrence of sufficient antimicrobial effect. The contact time can vary with concentration of the use compositions, method of applying the use compositions, temperature of the use compositions, pH of the use compositions, amount of the surface, liquid and/or product to be treated, amount of soil or substrates on/in the surface, liquid and/or product to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. In other embodiments, the exposure time is a few hours to days. The contact time will further vary based upon the concentration of peracid in a use solution.

The present methods can be conducted at any suitable temperature. In some embodiments, the present methods are conducted at a temperature ranging from about 0° C. to about 70° C., e.g., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms.

The present methods can be used to achieve any suitable reduction of the microbial population in and/or on the target or the treated target composition. In some embodiments, the present methods can be used to reduce the microbial population in and/or on the target or the treated target composition by at least one $\log_{10}$. In other embodiments, the present methods can be used to reduce the microbial population in and/or on the target or the treated target composition by at least two $\log_{10}$. In still other embodiments, the present methods can be used to reduce the microbial population in and/or on the target or the treated target composition by at least three $\log_{10}$.

The peroxycarboxylic acid compositions may include concentrate compositions or may be diluted to form use compositions. In general, a concentrate refers to a composition that is intended to be diluted with water to provide a use solution that contacts a surface, liquid and/or product in need of treatment to provide the desired cleaning, sanitizing or the like. The peroxycarboxylic acid composition that contacts the surface, liquid and/or product in need of treatment can be referred to as a concentrate or a use composition (or use solution) dependent upon the formulation employed in methods according to the invention. It should be understood that the concentration of the peroxycarboxylic acid in the composition will vary depending on whether the composition is provided as a concentrate or as a use solution.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Self-Accelerating Decomposition Test. As used herein, SADT refers to the lowest temperature at which self-accelerating decomposition may occur with the peracid composition. In some embodiments, SADT refers to the lowest temperature at which self-accelerating decomposition may occur under the commercial packaging, storage, transportation and/or use condition(s). SADT can be estimated, calculated, predicted and/or measured by any suitable methods. For example, SADT can be estimated, or measured directly by one of 3 methods (H1, H2 and H4) recommended by the UN Committee for the Transportation of Dangerous Goods in "Recommendations on the Transport of Dangerous Goods, Model Regulations" (Rev.17) ST/SG/AC.10/1/Rev.17. For example, the methodology disclosed in Malow and Wehrstedt, J. Hazard Mater., 120(1-3):21-4 (2005) can be used, which is herein incorporated by reference in its entirety.

The full test protocol used in this Example is available at "Recommendations on the Transport of Dangerous Goods," Manual of Tests and Criteria, 5th revised edition: (United Nations): Classification procedures, test methods and criteria relating to self-reactive substances of Division 4.1 and organic peroxides of Division 5.2: Test H.4 Heat accumulation storage test (28.4.4).

Since peroxycarboxylic acids fall into the organic peroxides classification and therefore are self-reactive, self-heating products, testing was conducted to demonstrate if cooling is required for a given package of a peroxycarboxylic acid product. One of the four published recommended methods of the UN Committee for the Transport of Dangerous Goods allows the modeling of a large volume package with Dewar flasks. Again, this method is utilized to model large commercial packages which if tested directly (i.e. with the $H_1$ method) might pose a significant hazard as well as inconvenience due to size. In this example the product was intended to be sold in 1000 L plastic tanks known as totes and it was necessary to determine if the SADT was greater or less than 45° C. If it was found to be less than 45° C. refrigeration would be required both in shipping and in storage and use thus severely limiting the products potential for a wide application in the marketplace. Additionally if the product has an SADT equal to or less than 50° C. the product is not permitted to be shipped stored or used in conatainers as large as 1000 L but is essentially limited to 200 L drums or smaller, again severely limiting the products applications A 1 L cylindrical Dewar flask is fitted with a closure that causes it to cool at the same rate as the 1000 L polyethylene tank. The Dewar flask is filled to 80% of full volume with the product, fitted with the specific closure and a recording thermometer, and is placed in an oven set at 45° C. Once the internal package temperature warms to 43° C. temperature, time recording is begun. If the temperature exceeds the oven temp of 45° C. by a magnitude of 6° C. (51° C.). before 7 days have elapsed the SADT for the product in that 1000 L package is defined as <45° C. and the product is deemed to require cooling. As such a requirement can severely limit use of a product in many industries, this SADT is considered an unfavorable property. If the temperature doesn't exceed a 6° C. rise over the oven temperature the SADT is deemed >45° C. and may be considered for shipping and storage in that 1000 L package without refrigeration.

The H4 test methodology was employed at 50° C. The tested peroxycarboxylic acid compositions are shown in Table 2.

TABLE 2

| | Wt % | |
| --- | --- | --- |
| Composition | DPA Formula | HEDP Formula |
| DPA | 0.05 | 0.0 |
| HEDP (60%) | 0.0 | 1.5 |
| Sulfonated oleic acid (70%) | 1-10 | 1-10 |
| Octanoic acid | 1-10 | 1-10 |
| Acetic acid | 2-20 | 2-20 |
| Sodium xylene sulfonate (40%) | 3-20 | 3-20 |
| Sodium cumene sulfonate (96%) | 1-5 | 1-5 |
| $H_2O_2$ (35%) | 10-50 | 10-50 |
| $Al_2(SO_4)_3 \cdot 18H_2O$ | 1-5 | 1-5 |
| $H_2SO_4$ (96%) | 12.5 | 12.5 |
| Deionized Water | 20-50 | 20-50 |
| Total | 100.0 | 100.0 |

The resulting SADT from the evaluated formulations is shown in FIG. 1. While the formulae were identical aside from their stabilizers, the DPA-stabilized peracid composition showed a much more gradual increase in temperature (below the SADT of the peracid) demonstrating suitability for stabilization for transportation and/or storage. In contrast, the phosphate/HEDP-stabilized peracid composition showed excessive increase in temperature in the first day, necessitating the termination of the experiment to avoid explosion of the composition/container. The results illustrate an advantage in DPA stabilization in a high acid environment.

Example 2

The methods of Example 1 were further employed to analyze the SADT of a fatty peracid, a peroxyoctanoic acid compositions having an even further increased acidity. While the formulae were identical aside from their stabilizers, the results again illustrate an advantage in DPA stabilization in a high acid environment that extends to fatty peracids such as peroxy octanoic acid.

TABLE 3

| | Wt % | |
| --- | --- | --- |
| Composition | HEDP Formula | DPA Formula |
| DPA | 0.0 | 0.05 |
| HEDP (60%) | 2.54 | 0.0 |
| Octanoic acid | 1-10 | 1-10 |
| Sodium octane sulfonate (40%) | 10-30 | 10-30 |
| $H_2O_2$ (35%) | 10-50 | 10-50 |
| $H_2SO_4$ (96%) | 14.14 | 14.14 |
| Deionized Water | 20-50 | 20-50 |
| Total | 100.0 | 100.0 |

Figure 2:
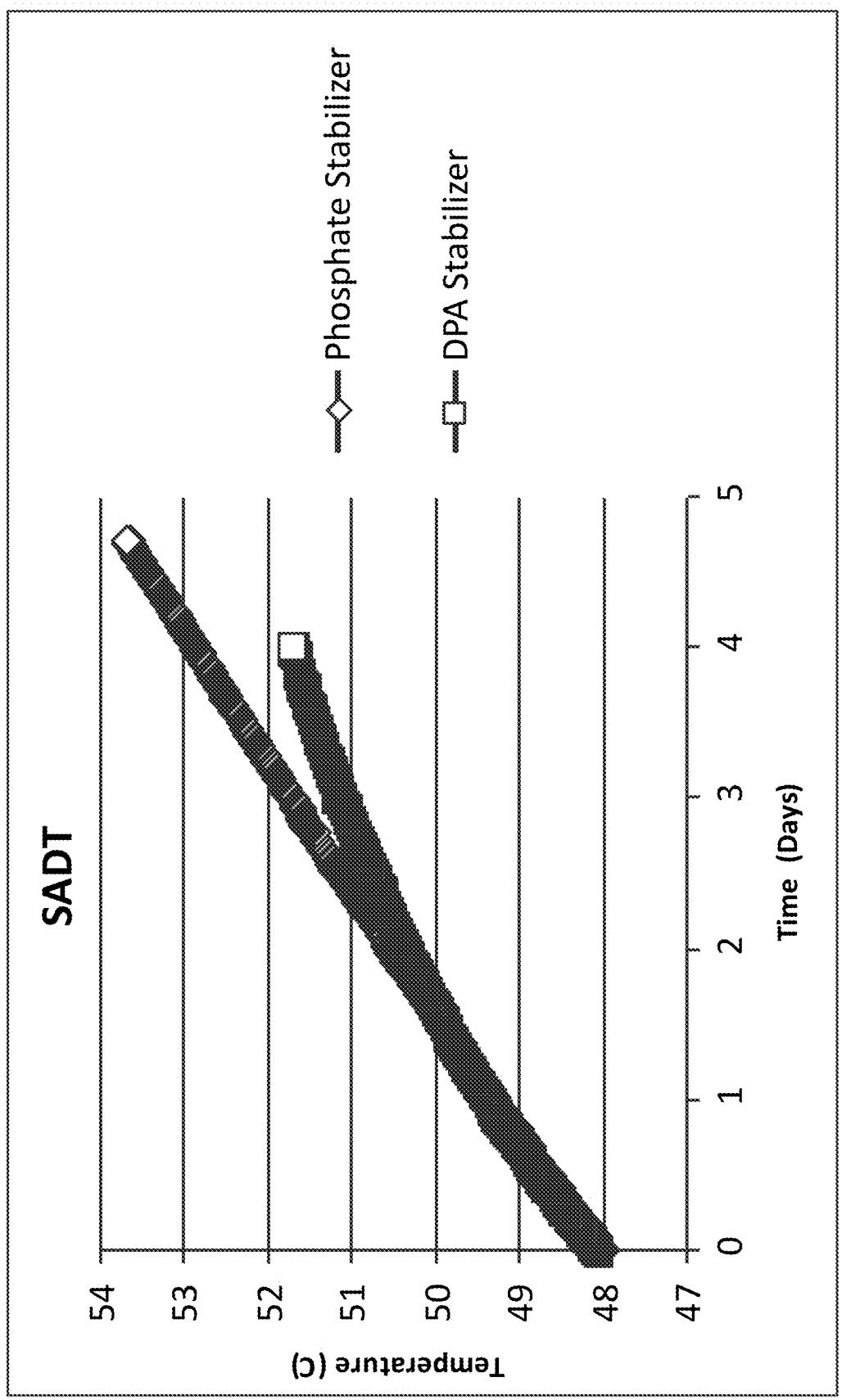
FIG. 2 shows a graph of the comparison of the SADT study of a DPA-stabilized, highly acidic peroxycarboxylic acid composition according to an embodiment of the invention with a phosphate based, highly acidic peroxycarboxylic acid composition.

The resulting SADT from the evaluated formulations is shown in FIG. 2. The DPA-stabilized peracid composition, even under increased acidity of the peracid composition, showed a much more gradual increase in temperature (below the SADT of the peracid) in comparison to the phosphate/HEDP-stabilized peracid composition. The DPA-stabilized peracid composition would likely meet DOT standards for transportation since its temperature projected out to 7 days since reaching 48° C. would likely not exceed 56° C.

Example 3

As set forth in Table 4 (and shown in FIG. 3) a strong acid containing a reduced hydrogen peroxide concentration was evaluated by the H4-SADT protocol in a Dewar flask modeling a 300 gallon IBC or plastic tote.

TABLE 4

| Composition | Wt % |
| --- | --- |
| DPA | 0.05 |
| HEDP (60%) | 0.0 |
| Sulfonated oleic acid (70%) | 1-10 |
| Octanoic acid | 1-10 |
| Acetic acid | 2-20 |
| Sodium xylene sulfonate (40%) | 1-5 |
| Sodium cumene sulfonate (96%) | 1-5 |
| $H_2O_2$ (35%) | 35 |
| $Al_2(SO_4)_3 \cdot 18H_2O$ | 0.05-2.0 |
| $H_2SO_4$ (96%) | 18 |
| Deionized Water | 20-50 |
| Total | 100.0 |

Figure 3:
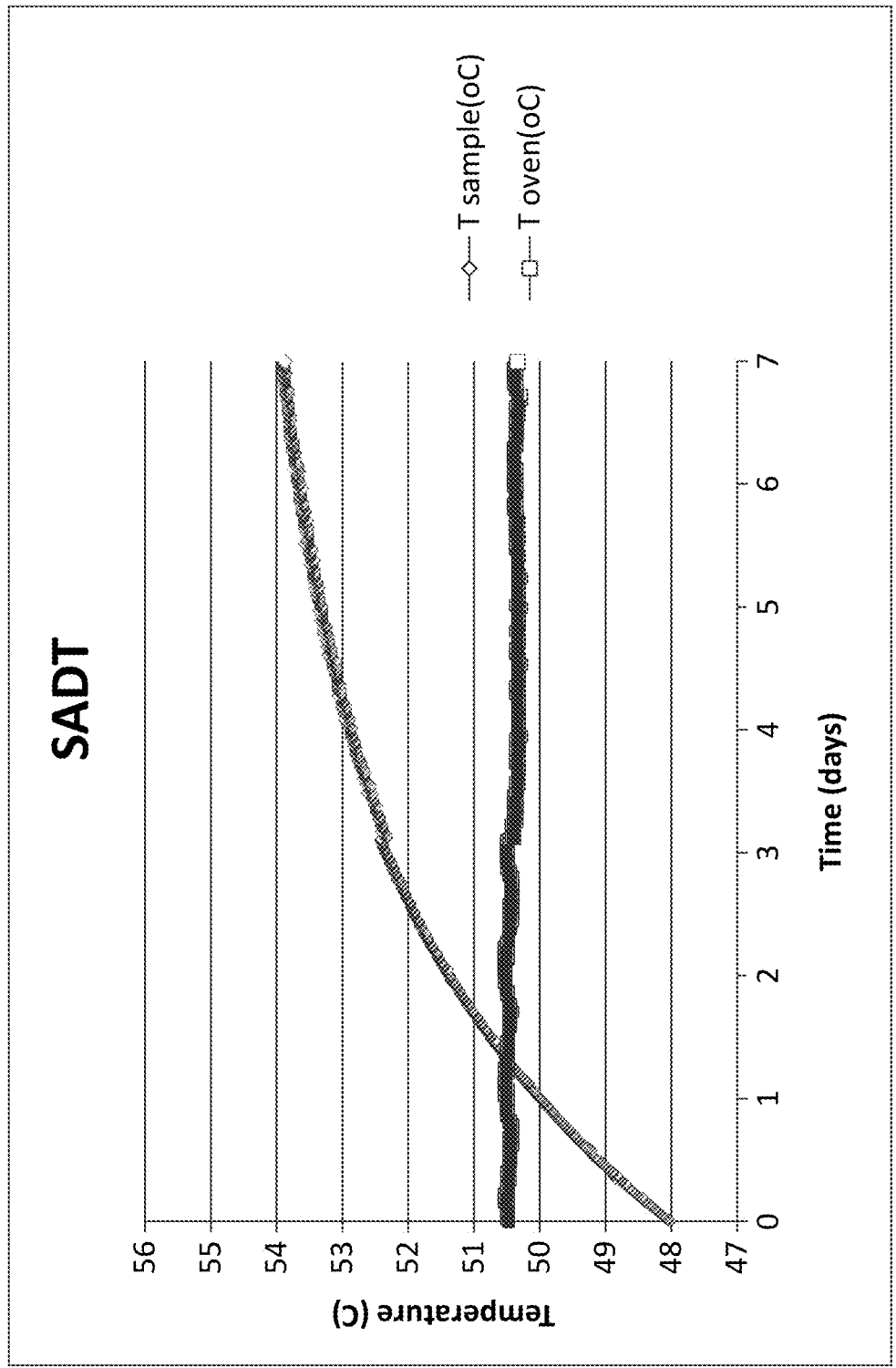
FIGS. 3-4 show graphs of the comparison of the SADT study of a highly acidic peracid composition, where the DPA-stabilizing agent according to embodiments of the invention provided sufficient stabilization, such that the self-heating effects were not sufficient to reach the oven temperature within the 7 day period.

The evaluation of the stability of the composition was conducted and despite the presence of the ~17% sulfuric acid, the composition containing the DPA stabilizing agent was stabilized. The stabilization of the composition, as shown in FIG. 3, illustrates the stabilization of the solution temperature only exceeding the 50° C. ambient temperature by 4.7° C. by day 7. Beneficially, these results qualify the highly acidic peracid composition for shipping and storage in a 300 gallon tote without refrigeration, demonstrating a significant improvement over the instability of HEDP-containing equivalent peracid compositions.

Example 4

The methods of Example 1 were further employed to analyze the SADT of a fatty peracid, a peroxyoctanoic acid compositions with an HEDP stabilizer, in comparison to an equivalent peracid composition with a DPA stabilizer, as shown in Table 5.

TABLE 5

| | Wt % | |
| --- | --- | --- |
| Composition | Formula HEDP stabilizer | Formula with DPA stabilizer |
| DPA | 0.0 | 0.05 |
| HEDP (60%) | 2.54 | 0.0 |
| Octanoic acid | 1-10 | 1-10 |
| Sodium octane sulfonate (40%) | 10-30 | 10-30 |
| H2O2 (35%) | 23.00 | 23.00 |
| H2SO4 (96%) | 14.14 | 14.14 |
| Deionized Water | 20-50 | 20-50 |
| Total | 100.0 | 100.0 |

Figure 4:
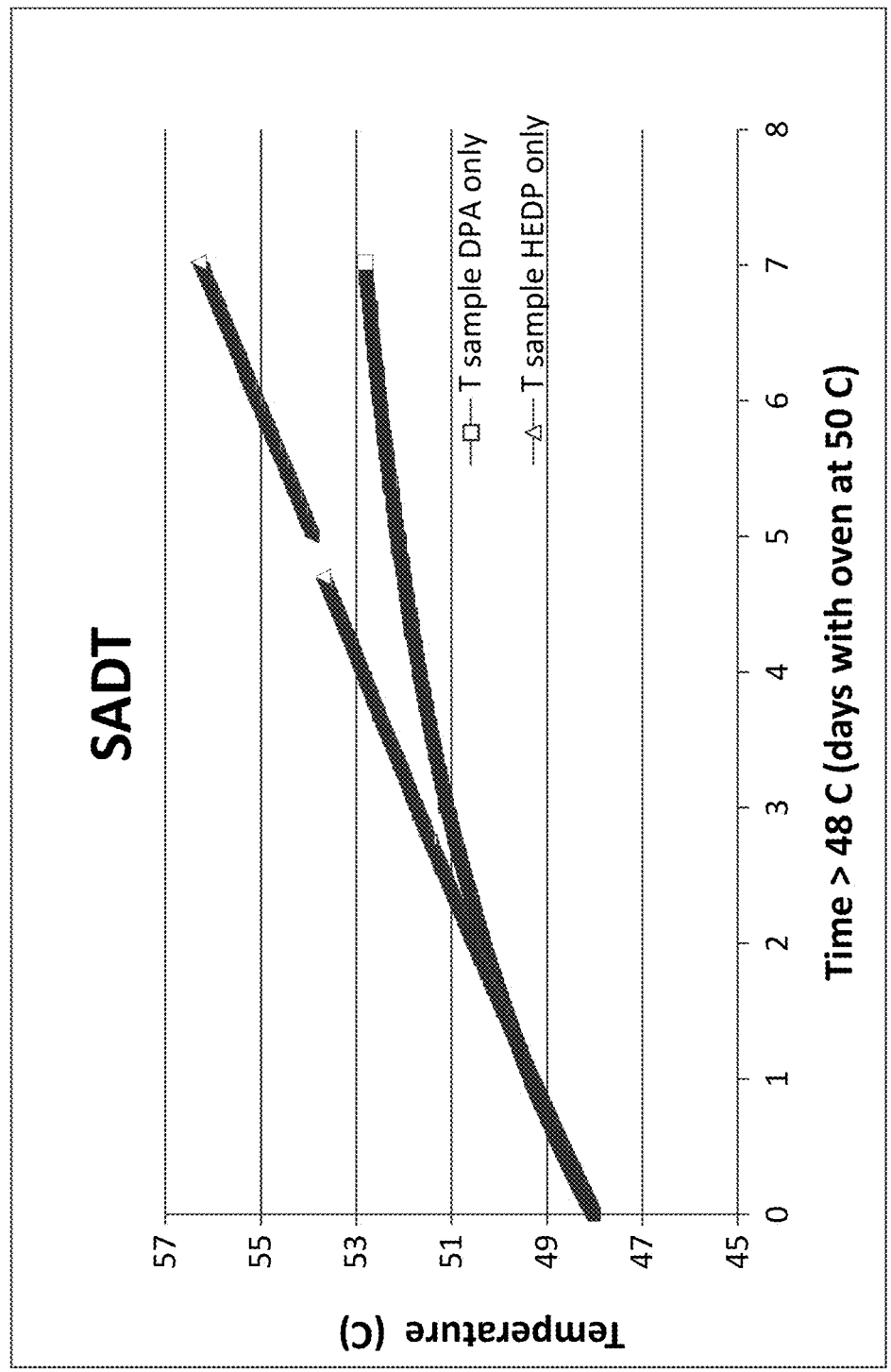

The evaluation of the stability of the composition was conducted and despite the presence of the ~14% sulfuric acid, the composition containing the DPA stabilizing agent according to embodiments of the invention was stabilized whereas the formula containing only an HEDP stabilizer failed prior to the 7$^{th}$ day. The stabilization of the composition, as shown in FIG. 4, illustrates the stabilization of the solution temperature only exceeding the 50° C. ambient temperature by 2.8° C. by day 7. Again, these results qualify the highly acidic peracid composition stabilized by the DPA stabilizing agent for shipping and storage in a 300 gallon tote without refrigeration. This demonstrates a significant improvement over the instability of HEDP-containing equivalent peracid compositions.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A stabilized homogenous equilibrium peracid composition comprising:
at least one of a straight or branched saturated aliphatic $C_2$-$C_{20}$ peroxycarboxylic acid;
at least one of a straight or branched saturated aliphatic $C_2$-$C_{20}$ carboxylic acid;

hydrogen peroxide;
from about 12.5 wt-% to about 50 wt-% of sulfuric acid; and
a peroxycarboxylic acid stabilizing agent, wherein the stabilizing agent is a picolinic acid or a compound having the following Formula (IA):

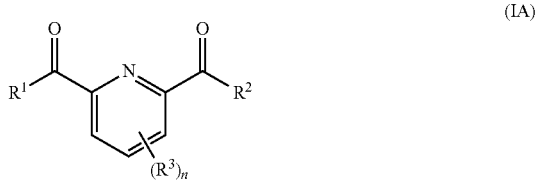

wherein $R^1$ is OH or $NR^{1a}R^{1b}$, wherein $R^{1a}$ and $R^{1b}$ are independently hydrogen or $(C_1-C_6)$alkyl; wherein $R^2$ is OH or $NR^{2a}R^{2b}$, wherein $R^{2a}$ and $R^{2b}$ are independently hydrogen or $(C_1-C_6)$alkyl; wherein each $R^3$ is independently $(C_1-C_6)$alkyl, $(C_2-C_6)$alkenyl or $(C_2-C_6)$alkynyl; and n is a number from zero to 3; or a salt thereof; or a compound having the following Formula (IB):

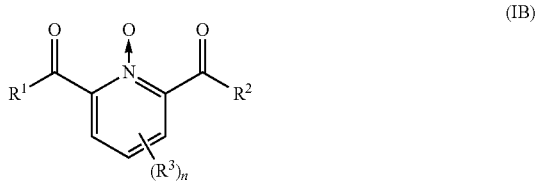

wherein R1 is OH or $NR^{1a}R^{1b}$, wherein $R^{1a}$ and $R^{1b}$ are independently hydrogen or $(C_1-C_6)$alkyl; wherein $R^2$ is OH or wherein $R^{2a}$ and $R^{2b}$ are independently hydrogen or $(C_1-C_6)$alkyl; wherein each $R^3$ is independently $(C_1-C_6)$alkyl, $(C_2-C_6)$alkenyl or $(C_2-C_6)$alkynyl;
and n is a number from zero to 3; or a salt thereof; and
wherein a use solution of said composition has a pH of below about 4, wherein at least about 80% of the $C_2-C_{20}$ peroxycarboxylic acid activity is retained after storage of at least 30 days at about 50° C., and wherein the composition has a self-accelerating decomposition temperature (SADT) of at least about 45° C.

2. The composition of claim 1, wherein the composition comprises from about 1 wt-% to about 40 wt-% of the $C_2-C_{20}$ peroxycarboxylic acid, from about 1 wt-% to about 80 wt-% of the $C_2-C_{20}$ carboxylic acid, from about 1 wt-% to about 80 wt-% of hydrogen peroxide, from about 12.5 wt-% to about 20 wt-% of the sulfuricmineral acid, and from about 0.01 wt-% to about 10 wt-% of the stabilizing agent.

3. The composition of claim 1, further comprising at least one additional agent selected from the group consisting of an anionic surfactant, a hydrotrope, a defoaming agent, a solvent, a fluorescent active agent and combinations thereof.

4. The composition of claim 1, wherein the composition has a ratio of hydrogen peroxide to the $C_2-C_{20}$ peroxycarboxylic acid from about 0.5:10 to about 10:0.5.

5. The composition of claim 1, wherein the peroxycarboxylic acid is peracetic acid and the composition further comprises one or more of a straight or branched saturated aliphatic $C_3-C_{20}$ peroxycarboxylic acid or a peroxysulfonated oleic acid.

6. The composition of claim 1, wherein the carboxylic acid is acetic acid and the composition further comprises one or more of a straight or branched saturated aliphatic $C_3-C_{20}$ carboxylic acid or a sulfonated oleic acid.

7. The composition of claim 1, wherein the stabilizing agent is 2,6-pyridinedicarboxylic acid, or a salt thereof.

8. The composition of claim 3, wherein the additional agent is a hydrotrope that aids solubilization of the stabilizing agent.

9. The composition of claim 1, wherein the composition retains at least about 85% of the $C_2-C_{20}$ peroxycarboxylic acid activity after storage of at least 30 days at about 50° C.

10. A method for reducing a microbial population using a stabilized homogenous equilibrium peroxycarboxylic acid composition comprising:
providing the peroxycarboxylic acid composition of claim 1; and
contacting a surface or substrate with a use solution of said composition for sufficient time to reduce a microbial population.

11. The method of claim 10, wherein the $C_2-C_{20}$ peroxycarboxylic acid is peroxyacetic acid and the composition further comprises peroxyoctanoic acid, peroxysulfonated oleic acid or a combination thereof, wherein the $C_2-C_{20}$ carboxylic acid is acetic acid and the composition further comprises octanoic acid, sulfonated oleic acid or a combination thereof, and wherein the stabilizing agent is 2,6-pyridinedicarboxylic acid, or a salt thereof.

12. The method of claim 10, wherein the surface or substrate is a food item, plant item, animal item, a container, an equipment, a system or a facility for growing, holding, processing, packaging, storing, transporting, preparing, cooking or serving the food item, plant item or the animal item, an instrument, a hard surface, a liquid media, equipment, a fabric surface, a fouled water or industrial processing liquid source, liquid system, or process water used in oil, gas and/or industrial processing operations.

13. The method of claim 10, wherein the contacting step lasts for at least 10 seconds and wherein the microbial population in and/or on the surface or substrate is reduced by at least two $\log_{10}$.

* * * * *

UNITED STATES PATENT AND TRADEMARK OFFICE
CERTIFICATE OF CORRECTION

PATENT NO. : 10,893,674 B2  
APPLICATION NO. : 15/019050  
DATED : January 19, 2021  
INVENTOR(S) : Junzhong Li, David D. McSherry and Richard Staub Page 1 of 1

It is certified that error appears in the above-identified patent and that said Letters Patent is hereby corrected as shown below:

In the Claims

In Column 35, Claim 1, Line 18:  
DELETE "$NR^{1a}R^{1b}$," before the second "wherein"  
INSERT -- -$NR^{1a}R^{1b}$,-- before the second "wherein"

In Column 35, Claim 1, Line 20:  
DELETE "$NR^{2a}R^{2b}$," after "or"  
INSERT -- -$NR^{2a}R^{2b}$,-- after "or"

In Column 35, Claim 1, Line 36:  
DELETE "R1" before "is"  
INSERT --$R^1$-- before "is"  
DELETE "$NR^{1a}R^{1b}$," before the second "wherein"  
INSERT -- -$NR^{1a}R^{1b}$,-- before the second "wherein"

In Column 35, Claim 1, Line 38:  
INSERT -- -$NR^{2a}R^{2b}$,-- before "wherein"

In Column 35, Claim 2, Line 53:  
DELETE "sulfuricmineral" before "acid"  
INSERT --sulfuric-- before "acid"

Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*